(12) United States Patent
Michal et al.

(10) Patent No.: US 11,590,329 B2
(45) Date of Patent: Feb. 28, 2023

(54) ALLERGIC RHINITIS DRUG DELIVERY IMPLANT

(71) Applicant: Spirox, Inc., Redwood City, CA (US)

(72) Inventors: Gene Michal, San Anselmo, CA (US); Daniel L. Cox, Palo Alto, CA (US); Piyush Arora, San Carlos, CA (US); Michael S. Mirizzi, San Jose, CA (US); Scott Baron, Menlo Park, CA (US)

(73) Assignee: Spirox, Inc., Maple Grove, MN (US)

( * ) Notice: Subject to any disclaimer, the term of this patent is extended or adjusted under 35 U.S.C. 154(b) by 146 days.

(21) Appl. No.: 16/414,212

(22) Filed: May 16, 2019

(65) Prior Publication Data

US 2019/0358439 A1 Nov. 28, 2019

Related U.S. Application Data

(60) Provisional application No. 62/672,477, filed on May 16, 2018.

(51) Int. Cl.
*A61M 31/00* (2006.01)

(52) U.S. Cl.
CPC ........ *A61M 31/002* (2013.01); *A61M 31/007* (2013.01); *A61M 2210/0681* (2013.01)

(58) Field of Classification Search
CPC .............. A61M 31/002; A61M 31/007; A61M 2210/0681; A61K 9/70; A61K 9/0092; A61K 9/0024; A61L 29/16; A61L 29/148
See application file for complete search history.

(56) References Cited

U.S. PATENT DOCUMENTS

| | | | |
|---|---|---|---|
| 4,351,337 A * | 9/1982 | Sidman | A61K 9/2045 424/424 |
| 6,447,522 B2 | 9/2002 | Gambale et al. | |
| 6,620,170 B1 * | 9/2003 | Ahern | A61B 17/0057 128/898 |
| 8,858,974 B2 | 10/2014 | Eaton et al. | |
| 2007/0134305 A1 * | 6/2007 | Zilberman | A61K 31/337 424/443 |
| 2008/0081064 A1 * | 4/2008 | Jelle | A61L 27/54 514/17.4 |
| 2010/0131043 A1 * | 5/2010 | Casas | A61M 31/002 623/1.15 |
| 2012/0027833 A1 * | 2/2012 | Zilberman | A61K 31/546 424/422 |
| 2014/0088347 A1 * | 3/2014 | Frigstad | A61F 2/0045 600/37 |
| 2015/0100133 A1 | 4/2015 | Xie et al. | |
| 2017/0056602 A1 * | 3/2017 | Medina | A61M 5/3287 |

OTHER PUBLICATIONS

Notification of Transmittal of the International Search Report and the Written Opinion of the International Searching Authority, or the Declaration issued in International Patent Application No. PCT/US2019/032638 dated Sep. 9, 2019.

* cited by examiner

*Primary Examiner* — Theodore J Stigell
*Assistant Examiner* — Robert F Allen
(74) *Attorney, Agent, or Firm* — McDonnell Boehnen Hulbert & Berghoff LLP

(57) ABSTRACT

In another example, a bioresorbable implant for use in a nasal region includes one or more bioresorbable polymers, and a pharmaceutical composition coupled to the one or more bioresorbable polymers. A release rate of the pharmaceutical composition is related to a degradation rate of the one or more bioresorbable polymers.

19 Claims, 12 Drawing Sheets

ALLERGIC RHINITIS DRUG DELIVERY IMPLANT

CROSS-REFERENCE TO RELATED APPLICATIONS

This application claims priority to U.S. Provisional Patent Application No. 62/672,477, filed May 16, 2018, the contents of which are hereby incorporated by reference in their entirety.

BACKGROUND

According to the *Allergic Rhinitis and its Impact on Asthma* (ARIA) 2016 guidelines, allergic rhinitis is one of the most common diseases globally and usually persists throughout life. Typical symptoms of allergic rhinitis are nasal itching, sneezing, rhinorrhea, and nasal congestion. Ocular symptoms include itching and redness of the eyes and tearing. Other symptoms include itching of the palate, postnasal drip, and cough. The burden and costs associated with allergic rhinitis are substantial. For example, allergic rhinitis reduces the quality of life of many patients, impairing sleep quality and cognitive function and causing irritability and fatigue. Additionally, it is a frequent reason for general practice office visits.

The World Allergy Organization (WAO) states that allergic rhinitis affects between 10% and 30% of adults and is the most common form of non-infectious rhinitis. In addition, the prevalence of allergic diseases is rising dramatically in both developed and developing countries. The World Health Organization has estimated that 400 million people in the world suffer from allergic rhinitis. In the United States, it affects 30 to 60 million individuals annually. Unfortunately, the care of patients with allergic diseases is fragmented and far from ideal. The WAO also highlights the need for better treatment adherence. Adherence to current treatment protocols is less than 50%, and the cost of non-adherence highly impacts the burden of chronic diseases worldwide.

Pharmacotherapy is the current mainstay of treatment for allergic diseases because it not only controls symptoms, but also improves the quality of life. Intranasal glucocorticosteroids are the most efficacious anti-inflammatory medication available for the treatment of allergic and non-allergic rhinitis. The rationale for using intranasal glucocorticosteroids in the treatment of allergic rhinitis is that high drug concentrations can be achieved at receptor sites in the nasal mucosa with a minimal risk of systemic adverse effects. Due to their mechanism of action, efficacy appears after 7-8 hours of dosing, but maximum efficacy may require up to 2 weeks to develop. They are effective for all nasal symptoms, ocular symptoms, polyposis and sinusitis.

Multiple intranasal steroids have been approved by the United States Food and Drug Administration, and many are available over-the-counter. Such steroids include beclomethasone, budesonide, ciclesonide, flunisolide, fluticasone furoate, fluticasone propionate, mometasone furoate and triamcinolone acetonide. Despite the range of topical potency, lipid solubility, and binding affinity, there are no significant differences in efficacy between the available agents. The continuous use of intranasal steroids is recommended and more efficacious than intermittent use, but studies of as-needed use of intranasal fluticasone have shown that intermittent use is still better than placebo. These steroids may also be useful in the treatment of some forms of nonallergic rhinitis.

Intranasal steroid sprays like Nasonex (mometasone furoate) and Flonase (fluticasone propionate) are aqueous suspensions delivered using a spray pump into the nasal passages. Each spray delivers 50 micrograms of steroid and a standard dose is 2 sprays in each nostril once daily. This provides a total daily dose of 200 micrograms of drug. However, a large amount of the administered drug is swallowed and undergoes first-pass metabolism, and only a small fraction crosses the nasal mucosa.

A short course of oral corticosteroids may be appropriate for the treatment of very severe or intractable nasal symptoms or to treat significant nasal polyposis. However, single administration of parenteral corticosteroids is discouraged, and recurrent administration of parenteral corticosteroids is contraindicated, because of greater potential for long-term corticosteroid side effects. Additionally, short courses of systemic corticosteroids have not been shown to be superior to intranasal steroids.

When oral therapy is not feasible, an intramuscular injection can be given. The suggested initial dose is 60 mg triamcinolone acetonide injected deeply into the gluteal muscle. An injection of a steroid suspension, such as Kenalog-40, can be administered directly into the inferior turbinate. The total dose used is commonly 40 mg. Half of the dose is administered into each inferior turbinate. A total dose of 20 mg has also been described. Intraturbinal steroid injections are thought to have the efficacy of oral steroids, while lacking their side effect profile. There is some evidence that intraturbinal injections are more effective than intramuscular injections.

Currently available therapies are summarized in Table 1. Each of these therapies has significant disadvantages that limit patient satisfaction.

TABLE 1

| Current Allergic Rhinitis Therapy | Disadvantages |
| --- | --- |
| Oral steroids | Non-compliance, systemic side effects, dose tapering |
| Depot injection steroids | Systemic side effects |
| Intranasal steroids | Non-compliance, nose bleeds |
| Leukotriene receptor antagonists | Less effective than steroids, non-compliance |
| Oral antihistamines | Less effective than steroids, systemic side effects |
| Intranasal antihistamines | Non-compliance, systemic side effects, nose bleeds |
| Decongestants | Non-compliance, systemic side effects, symptom rebound |
| Immunotherapy | Non-compliance, lengthy treatment regimen, expensive |

U.S. Pat. No. 9,480,828 by Reif, et al. described a drug eluting implant that is implanted into an inferior turbinate. The method includes creation of a pocket in the inferior turbinate to place one or more implants containing a therapeutic compound.

U.S. Patent Application Publication No. 2017/0056602 by Medina, et al. describe implants that are placed in turbinate mucosal tissue. The implants may be biodegradable and delivered via a needle. Medina describes a device and method for inserting a needle submucosally into turbinate tissue, one or more drug eluting solid implants disposed within the hollow needle which contain a mucosal engaging feature, activating the actuator to deliver one or more implants from the needle into the soft tissue and bury at least one tissue engaging feature within the tissue.

What is needed, therefore, is a locally delivered, sustained drug release implant for the nasal passages that safely relieves the symptoms of allergic rhinitis.

SUMMARY

Described herein is an implant for use in the nasal region to deliver a sustained release of a pharmacologic agent for the treatment of patients with allergic rhinitis symptoms. The implant can elute steroid to treat allergic rhinitis symptoms without the need to create a pocket in the tissue first. The implant can be placed in an out-patient setting by delivering an implant through a needle or delivering a self-piercing implant using a delivery device. The implant can elute the pharmacologic agent over a long period of time (e.g., 30 days or more).

In an example, a method of treating tissue in a nasal cavity includes inserting a bioresorbable implant into a soft tissue of a nasal cavity. The implant comprises one or more biodegradable polymers, and a pharmaceutical composition coupled to the one or more biodegradable polymers. The method also includes after inserting the bioresorbable implant into the soft tissue of the nasal cavity, releasing the pharmaceutical composition from the one or more biodegradable polymers. The one or more biodegradable polymers are configured to control a release rate of the pharmaceutical composition over time.

In another example, a bioresorbable implant for use in a nasal region includes one or more bioresorbable polymers, and a pharmaceutical composition coupled to the one or more bioresorbable polymers. A release rate of the pharmaceutical composition is related to a degradation rate of the one or more bioresorbable polymers.

In another example, a system includes a bioresorbable implant and a delivery device. The bioresorbable implant includes one or more bioresorbable polymers, and a pharmaceutical composition coupled to the one or more bioresorbable polymers. A release rate of the pharmaceutical composition is related to a degradation rate of the one or more bioresorbable polymers. The delivery device is configured to insert the bioresorbable implant in soft tissue of a nasal cavity.

The features, functions, and advantages that have been discussed can be achieved independently in various examples or may be combined in yet other examples further details of which can be seen with reference to the following description and drawings.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative examples, in which the principles of the invention are utilized, and the accompanying drawings of which:

DETAILED DESCRIPTION

Disclosed examples will now be described more fully hereinafter with reference to the accompanying drawings, in which some, but not all of the disclosed examples are shown. Indeed, several different examples may be described and should not be construed as limited to the examples set forth herein. Rather, these examples are described so that this disclosure will be thorough and complete and will fully convey the scope of the disclosure to those skilled in the art.

Described herein is a bioresorbable implant for use in a nasal region of a patient that can deliver a sustained release of one or more pharmaceutical compositions (e.g., a corticosteroid drug) to the cells/tissues for reduction of the symptoms of a disease state (e.g., allergic rhinitis) and/or for bulking and/or stiffening the cells/tissues (e.g., nasal airway obstruction). Within examples, the bioresorbable implant can be placed in a nasal passage, such as in an inferior turbinate, a middle turbinate, a superior turbinate, a wall of an osteomeatal complex, in or under a septal mucosa, or in or near polyps. The bioresorbable implant can release a sufficient quantity of the drug(s) to treat the disease state over a period of time (e.g., relieve rhinitis symptoms over a period of weeks to months).

The bioresorbable implant can, for example, alleviate the inconvenience and non-compliance associated with steroid nasal sprays. Additionally, since the pharmaceutical composition(s) are delivered locally, one or more systemic side effects of the pharmaceutical composition(s) can be reduced (or minimized). While and/or after the pharmaceutical composition(s) are released, the bioresorbable implant can be absorbed into a body of the patient, enabling the procedure to be repeated as needed. Within examples, the bioresorbable implant can release the pharmaceutical composition(s) at a release rate that is based, at least in part, on a degradation rate of one or more bioresorbable polymers of the bioresorbable implant. Also, within examples, the bioresorbable implant can include one or more features that additionally or alternatively assist in controlling the release rate of the pharmaceutical composition.

Within examples, the bioresorbable implant can be made from materials that are biocompatible. This biocompatibility can be achieved by a bioresorbable nature of material(s) of the bioresorbable implant. Bioresorbability in this respect means that the material(s) can be broken down by, and be cleared from the body and do not require mechanical removal.

Figure 1:
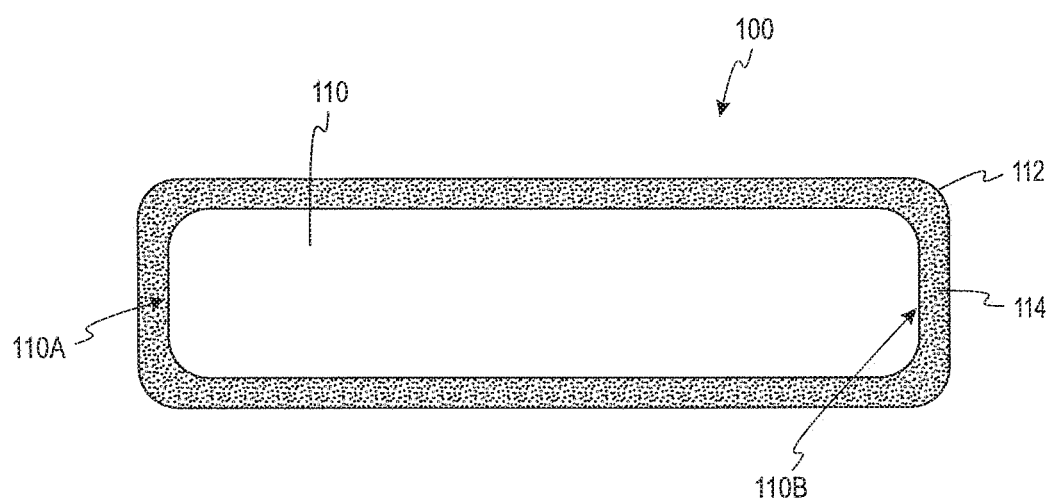
FIG. 1 shows a bioresorbable, nasal implant having a drug-eluting coating thereon, according to an example.

Referring to FIG. 1, a bioresorbable implant 100 is shown according to an example. As shown in FIG. 1, the bioresorbable implant 100 includes a polymeric bioresorbable substrate 110 coated with a bioresorbable polymeric coating 112 containing a pharmaceutical composition 114 (e.g., which is retained within a coating matrix of the bioresorbable polymeric coating 112). Within examples, the pharmaceutical composition 114 can include one or more drugs (e.g., a corticosteroid) and/or one or more therapeutic agents within a coating matrix of the coating 112.

In one example, the polymeric bioresorbable substrate 110 can be a solid, elongated rod that extends from a first end 110A of the polymeric bioresorbable substrate 110 to a second end 110B of the polymeric bioresorbable substrate 110. In another example, the polymeric bioresorbable substrate 110 can be a tube having a through-bore extending from the first end 110A to the second end 110B.

In one example, a cross-sectional shape of the polymeric bioresorbable substrate 110 can be a circular shape (e.g., the rod can be a solid, elongated cylinder). However, in other examples, the polymeric bioresorbable substrate 110 can have a different cross-sectional shape (e.g., the cross-section can have an oval shape, a square shape, a rectangle shape, a pentagon shape, a hexagon shape, an octagon shape, a polygonal shape, and/or a non-polygonal shape). Within examples, the cross-sectional shape can be selected from a plurality of potential shapes based on one or more criteria including a particular type of tissue to be targeted and/or a shape of a nasal cavity of a patient to be treated.

The bioresorbable implant 100 (e.g., a combination of the polymeric bioresorbable substrate 110 and the coating 112) can be configured to be inserted into the soft tissue of the turbinates via a delivery needle and plunger system, as described further below. For example, the bioresorbable implant 100 can have a diameter of 1 millimeter (mm) or less, and the bioresorbable implant 100 can have a length (i.e., in a dimension along an axis between the first end 110A and the second end 110B) from 3 mm to 25 mm. The delivery needle can be 16 gauge or smaller (i.e., higher gauge number). In one example, the bioresorbable implant 100 can be implanted fully into the turbinate (e.g., an entirety of the bioresorbable implant can be positioned in the turbinate tissue). In another example, the bioresorbable implant 100 can stick out partially into the nasal passage (e.g., a first portion of the bioresorbable implant 100 can be in the turbinate and a second portion of the bioresorbable implant 100 extend from the turbinate into the mucosa), which can allow the pharmaceutical composition 114 to elute into the nasal mucosa and/or mucous on the nasal mucosa.

In an example, the bioresorbable polymeric coating 112 of bioresorbable implant 100 can be configured to elute the pharmaceutical composition 114 for a period of 2 weeks to 5 months. Concurrently, the coating 112 and underlying substrate 110 can be configured to degrade by ester hydrolysis.

As noted above, the pharmaceutical composition 114 can include one or more drugs and/or one or more therapeutic agents. As an example, the drug(s) of the pharmaceutical composition 114 can include a corticosteroid such as, for example, beclomethasone, budesonide, ciclesonide, flunisolide, fluticasone fuorate, fluticasone propionate, mometasone, triamcinolone, dexamethasone, fluocinolone acetonide, clobetasol, methylprednisolone, and/or mometasane furoate. As examples, the therapeutic agent(s) can include an antioxidant, anti-inflammatory agent, antimicrobial agent, antiangiogenic agent, anti-apoptotic agent, vascular endothelial growth factor inhibitor, antiviral agent, calcineurin inhibitor, antihistamine, mast cell stabilizing agent, and/or immunomodulator.

The polymeric bioresorbable substrate 110 can be composed, for example, of phosphorylcholines, phosphorylcholine linked macromolecules, polyesters, polyanhydrides, polyphosphazenes, poly(lactide-co-glycolides) (PLGA), polylactic acids (PLA), poly(hydroxybutyrates), poly(hydroxybutyrate-co-valerates), polydioxanones (PDO), polyorthoesters, polyglycolic acids (PGA), polycaprolactones (PCL), poly(glycolic acid-co-trimethylene carbonates), polyphosphoesters, polyphosphoester urethanes, poly (amino acids), poly(trimethylene carbonate), poly(iminocarbonate), polyalkylene oxalates, polyiminocarbonates, aliphatic polycarbonates, fibrins, fibrinogens, starches, collagens, polycarbonate urethanes, PCL-co-PEG, PLA-co-PEG-polyamides, copolymers thereof, polymer derivatives thereof, and combinations thereof. One specific example is Evonik Resomer LR 704S, an L, DL-PLA (70% L, 30% DL), which can last up to a year or more in vivo. Examples of shorter duration polymers are copolymers of lactic and glycolic acids (PLGA). Service life can be tuned by altering ratios of lactide to glycolide, as displayed in Table 2 below:

TABLE 2

DURECT ® LACTEL PLGA CO-POLYMERS

| Ratio | Polymer | Inherent Viscosity (dL/g) | Approximate Resorption Time (months) |
| --- | --- | --- | --- |
| 50:50 | DL-PLG | 0.55-0.75 | 1-2 |
| 65:35 | DL-PLG | 0.55-0.75 | 3-4 |
| 75:25 | DL-PLG | 0.55-0.75 | 4-5 |
| 85:15 | DL-PLG | 0.55-0.75 | 5-6 |

The various service lives of different bioresorbable polymers can allow for tailoring a degradation rate of the coating 112 versus a degradation rate of the underlying substrate 110. Accordingly, in some examples, one or more bioresorbable polymers of the polymeric bioresorbable substrate 110 can be different than one or more bioresorbable polymers of the coating 112. Alternatively, in other examples, the polymer(s) of the polymeric bioresorbable substrate 110 can be the same as the polymer(s) of the coating 112 and the polymeric bioresorbable substrate 110. As examples, the polymeric bioresorbable substrate 110 can be injection molded, compression molded, cast, and/or machined from a relatively larger block of the polymer.

In one example, the bioresorbable implant 100 can include the polymeric bioresorbable substrate 110 in the form of a rod having a diameter of 0.8 mm and a length of 20 mm length, and which is injection molded using Durect Lactel 50:50DL-PLG with an inherent viscosity of 0.55-0.75 dL/g. In this example, the coating 112 can be made from the same polymer, using a mixture of true solvents and non-solvents, for example, 30% ethyl acetate and 5% anisole (true solvents for PLGA) with 65% cyclohexane (a non-solvent), along with a corticosteroid (e.g. mometasone furoate). Drug to polymer ratios can range from 1:10 to 1.5:1. Non-solvent can be included to reduce the solvent penetration of the coating 112 into the polymeric bioresorbable substrate 110, to avoid rod softening and solvent retention. The polymeric bioresorbable substrate 110 can be dip coated with the drug-polymer formulation, or syringe-coated, a process in which the coating is dispensed from a syringe via a Harvard syringe pump or similar apparatus while the polymeric bioresorbable substrate 110 rotates and traverses in front of the syringe tip. The polymeric bioresorbable substrate 110 may also be sprayed with the drug-polymer coating. If the drug to polymer ratio is 7:8 and the coating is syringe coated onto the polymeric bioresorbable substrate 110 at a total added non-volatile weight of 1.5 mg, then 0.7 mg or 700 µg drug will be in place on the polymeric bioresorbable substrate 110. If the drug to polymer ratio is 1:2 and the added weight is 2.1 mg, then 700 µg drug would once again be present on the polymeric bioresorbable substrate 110. 700 µg represents the equivalent of 35 doses at 20 µg/dose.

Within examples, the bioresorbable implant 100 can additionally or alternatively include the pharmaceutical composition 114 in the polymeric bioresorbable substrate 110. For instance, in some examples, the pharmaceutical composition 114 can be co-compression molded with a polymeric material of the polymeric bioresorbable substrate 110, and then the polymeric bioresorbable substrate 110 can be coated with the coating 112. In these examples, the pharmaceutical composition 114 can be delivered to a target tissue of the patient via the coating 112 and the polymeric bioresorbable substrate 110.

In some implementations, the pharmaceutical composition 114 in the polymeric bioresorbable substrate 110 can be the same as the pharmaceutical composition 114 of the coating 112. In other implementations, the pharmaceutical composition 114 in the polymeric bioresorbable substrate 110 can be different as the pharmaceutical composition 114 of the coating 112. For instance, in one implementation, the pharmaceutical composition 114 in the polymeric bioresorbable substrate 110 can include the drug(s) and/or the therapeutic agent(s), whereas the coating 112 can omit the drug(s). As such, in this implementation, the coating 112 can be a drug-free coating (e.g., degradable polyester) that inhibits a burst release of the pharmaceutical composition 114 in the polymeric bioresorbable substrate 110.

In other examples, the bioresorbable implant 100 can omit the separate coating 112 such that the bioresorbable implant 100 delivers the pharmaceutical composition 114 from only the polymeric material of the polymeric bioresorbable substrate 110. Drug release in such a case can be governed by a combination of initial burst release, Fickian diffusion of the hydrophobic drug through the polymer matrix, and drug release from polymer degradation. Lower glass transition temperature (Tg) co-polymers, such as those containing caprolactone or tri-methylene carbonate, can be molded at lower temperatures (90°–110° C.) and assist forming the drug-polymer composite without degrading the drug.

In some implementations in which the polymeric bioresorbable substrate 110 is co-compressed with the pharmaceutical composition 114, the polymeric bioresorbable substrate 110 can include a plurality of different zones each having different degradation rate. For example, the polymeric bioresorbable substrate 110 can include a plurality of fused segments, with each segment being formed from a different co-polymer with a different respective degradation rate. In one example, the different segments of the polymeric bioresorbable substrate 110 can be molded individually, cut into segments, and then assembled via butt-joints adhered with heat and/or a degradable polyester adhesive solution.

In some implementations, the bioresorbable implant 100 can be particularly efficacious when the bioresorbable implant 100 is configured to initially release the pharmaceutical composition 114 at a relatively high release rate for a first portion of a dosage period of time, and then release the pharmaceutical composition at a relatively lower (sustained) release rate for a second portion of the dosage period of time. The relatively high release rate can be beneficial in mitigating relatively severe symptoms, and the relatively lower release rate can be beneficial in mitigating reoccurrence of the symptoms. In an example, the bioresorbable implant 100 can be configured to provide a plurality of different release rates by providing the polymeric bioresorbable substrate 110 with the plurality of different zones having the different degradation rates.

Figure 2:
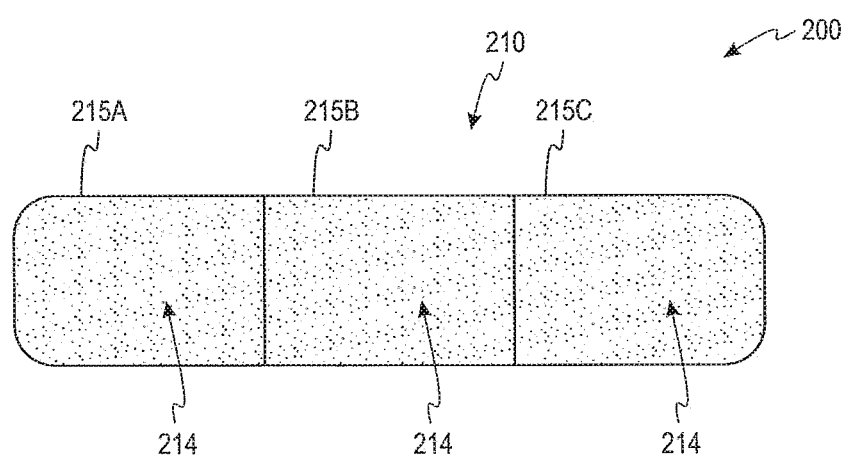
FIG. 2 shows a bioresorbable, nasal implant, according to another example.

Referring to FIG. 2, a bioresorbable implant 200 is shown according to an example. As shown in FIG. 2, the bioresorbable implant 200 includes a polymeric bioresorbable substrate 210 including a plurality of different segments 215A-215C, which each have a different degradation rate.

In FIG. 2, the plurality of segments 215A-215C include a first segment 215A, a second segment 215B, and a third segment 215C. The first segment 215A is made from a first polymer having a first degradation rate, the second segment 215B is made from a second polymer having a second degradation rate, and the third segment 215C is made from a third polymer having a third degradation rate. In this example, the first polymer, the second polymer, and the third polymer are different from each other such that the first degradation rate, the second degradation rate, and the third degradation rate are different from each other. The first polymer, the second polymer, and the third polymer can be respective ones of the polymers described above with respect to the polymeric bioresorbable substrate 110.

The first segment 215A is coupled to a first side of the second segment 215B, and the third segment 215C is coupled to a second side of the second segment 215B. In this example, the first segment 215A, the second segment 215B, and the third segment 215C all include a pharmaceutical composition 214. The pharmaceutical composition 214 can include one or more drugs and/or one or more therapeutic agents such as the drug(s) and/or therapeutic agent(s) described above with respect to the pharmaceutical composition 114 show in FIG. 1. As the release rate of the pharmaceutical composition 214 is related to the respective degradation rate of each segment 215A-215C, the bioresorbable implant 200 can release the pharmaceutical composition 214 at a plurality of release rates, which are different from each other, when the segments 215A-215C include a plurality of different biodegradable polymers with different degradation rates.

Although the polymeric bioresorbable substrate 210 includes three segments 215A-215C in FIG. 2, the polymeric bioresorbable substrate 210 can include a lesser quantity of segments 215A-215C (i.e., two segments) or a greater quantity of segments 215A-215C (i.e., more than three segments) in other examples. Additionally, although a size of each segment 215A-215C is approximately equal to each other in FIG. 2, one or more of the segments 215A-215C can have a size that is different than a size of another of the segments 215A-215C. This can help to further control the release of the pharmaceutical composition 214 over a dosage period of time.

In some implementations, the pharmaceutical composition 214 can be the same for all of the segments 215A-215C. In other implementations, the pharmaceutical composition 214 of one or more of the segments 215A-215C can be different than the pharmaceutical composition 214 of another one of the segments 215A-215C. This can allow the bioresorbable implant 200 to deliver a plurality of different drug(s) and/or therapeutic agent(s) at one or more dosage rates (e.g., due to the different degradation rates) and/or over one or more dosage periods of time.

Figure 3:
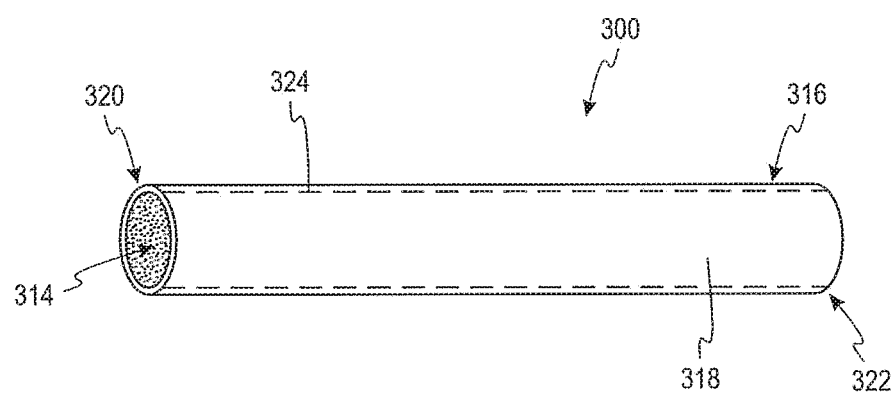
FIG. 3 shows a bioresorbable, nasal implant including a bioresorbable tube with a drug therein, according to an example.

Referring to FIG. 3, a bioresorbable implant 300 is shown according to another example. The bioresorbable implant 300 includes a porous bioresorbable tube 316 and a pharmaceutical composition 314. As shown in FIG. 3, the porous bioresorbable tube 316 includes a sidewall 318 that extends from a first end 320 of the porous bioresorbable tube 316 to a second end 322 of the porous bioresorbable tube 316. Additionally, the sidewall 318 defines an interior bore 324 that extends from the first end 320 to the second end 322.

The pharmaceutical composition 314 is in the interior bore 324 of the porous bioresorbable tube 316. In one example, the pharmaceutical composition 314 can completely fill the interior bore 324 of the porous bioresorbable tube 316. In another example, the pharmaceutical composition 314 can partially fill the interior bore 324. Within examples, the pharmaceutical composition 314 can include one or more drugs and/or one or more therapeutic agents such as, for instance, the drug(s) and/or therapeutic agent(s) described above and below.

The porous bioresorbable tube 316 can be configured to control the release of the pharmaceutical composition 314 from the interior bore 324. For example, the porous bioresorbable tube 316 can be formed from a polymer (e.g., the polymers described above), and a release rate of the pharmaceutical composition 314 can be related to a degradation rate of the polymer of the porous bioresorbable tube 316. A variety of polymers can be used for the porous bioresorbable tube 316 depending on the desired degradation time and release rate. As some examples, the porous bioresorbable tube 316 can be made of poly-L-lactide (PLLA), polymer D-lactic acid (PDLA), PLGA, PCL, or a combination thereof.

Since most corticosteroids are poorly soluble in water, an aqueous concentration of the pharmaceutical composition 314 at an inside surface of the porous bioresorbable tube 316 can remain relatively constant over an extended period of time. To increase the release rate of the pharmaceutical composition 314, the porous bioresorbable tube 316 itself can be loaded with drug in a matrix (e.g., as described above with respect to the polymeric bioresorbable substrate 110 that is co-compressed with the pharmaceutical composition 114). This can enable the pharmaceutical composition 314 in the matrix of the porous bioresorbable tube 316 to be released faster than the pharmaceutical composition 314 in the interior bore 324 of the porous bioresorbable tube 316, and leaves channels in the polymer that enable the pharmaceutical composition 314 in the interior bore 324 of the porous bioresorbable tube 316 to be released more quickly.

The physical properties of the pharmaceutical composition 314, such as its solubility, may further influence the release rate of the pharmaceutical composition 314. For example, mometasone furoate is much less soluble than triamcinolone acetonide. In addition to the pharmaceutical composition 314, the porous bioresorbable tube 316 can further include one or more preservatives and/or processing agents therein as desired. The preservative(s) can help to prolong a lifespan of the pharmaceutical composition 314. The processing agent(s) can help to aid in delivering the pharmaceutical composition 314 to a target tissue.

In one example, the porous bioresorbable tube 316 can have a length between approximately 1 centimeter (cm) and approximately 3 cm, and a diameter between approximately 0.5 mm and approximately 1.0 mm. In other examples, the porous bioabsorable tube 316 can have a different length and/or a different diameter based on a dose of the pharmaceutical composition 314 to be delivered.

In FIG. 3, the first end 320 and the second end 322 of the porous bioresorbable tube 316 are respective annular openings defined by the sidewall 318 of the porous bioresorbable tube 316. However, in other examples, the first end 320 and/or the second end 322 can be configured differently. For instance, in another example, the bioresorbable implant 100 can include one or more caps (not shown) that are coupled to the sidewall 318 at the first end 320 and/or the second end 322. A material of the caps can be the same as or different than the material of the porous bioresorbable tube 316. In some examples, the cap(s) can be coupled to the first end 320 and/or the second end 322 of the porous bioresorbable tube 316 with a solvent binding.

Figure 4:
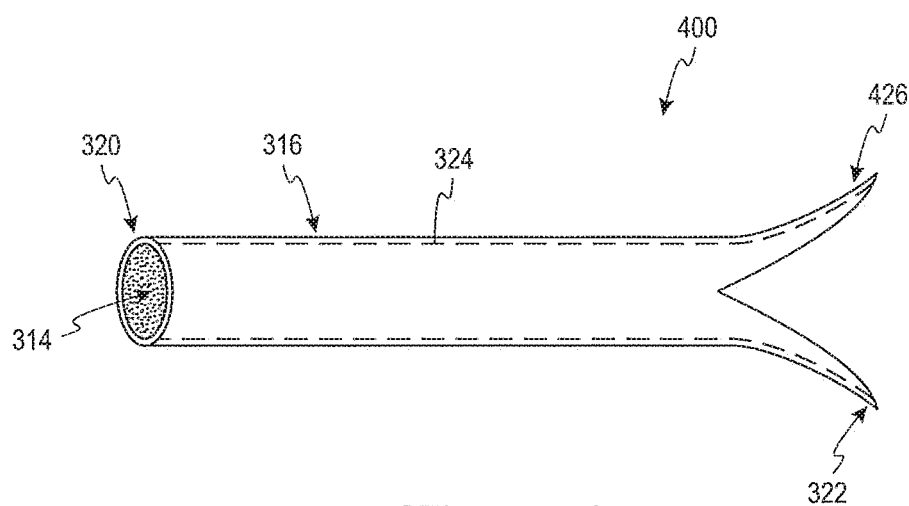
FIG. 4 shows a bioresorbable, nasal implant having a flared end, according to an example.

As another example, one of the first end 320 or the second end 322 can be configured to assist in retaining the bioresorbable implant 300 at an implantation site. For instance, FIG. 4 shows a bioresorbable implant 400 that substantially similar or identical to the bioresorbable implant 300 of FIG. 3, except the bioresorbable implant 400 includes a retention feature 426 at one end (e.g., the second end 322) of the porous bioresorbable tube 316 to help hold the bioresorbable implant 400 in place at the implantation site. Specifically, in FIG. 4, the retention feature 426 is shown as a flared or forked feature having a cross-sectional shape that increases along a direction from the first end 320 to the second end 322. Implants with such features are described in International Application No. PCT/US2017/68419, filed Dec. 26, 2017, the entirety of which is incorporated by reference herein.

Figure 5:
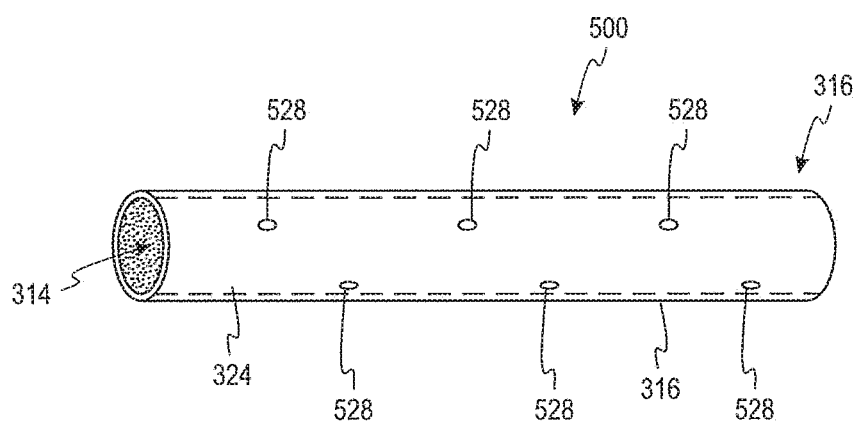
FIG. 5 shows a bioresorbable, nasal implant having a plurality of apertures therethrough for drug delivery, according to an example.

In FIGS. 3-4, the porous bioresorbable tube 316 includes a plurality of pores through which the pharmaceutical composition 314 can be released to the target tissue. In such examples, a release rate of the pharmaceutical composition 314 can be based on the degradation rate of the porous bioresorbable tube 316 and the pores of the bioabsorable tube 316 (e.g., a size and/or a quantity of the pores). However, in other examples, the bioresorbable implants 300, 400 can release the pharmaceutical composition 314 through one or more apertures through the sidewall 318 of the porous bioresorbable tube 316. As an example, FIG. 5 shows a bioresorbable implant 500 that can be substantially similar or identical to the bioresorbable implants 300, 400 of FIG. 3-4, except the bioresorbable implant 500 further includes a plurality of apertures 528 in the sidewall 318. In some examples, the aperture(s) 528 can be completely open from an interior (e.g., the interior bore 324) to an exterior of the porous bioresorbable tube 316. In other examples, the aperture(s) 528 can be covered with a polymer that influences (e.g., slows down) the release rate of the pharmaceutical composition 314.

In FIG. 5, a release rate of the pharmaceutical composition can be based on a quantity of the apertures 528, a size of the apertures 528, a thickness of the sidewall 318, and/or a degradation rate of the porous bioresorbable tube 316. The release rate can additionally or alternatively be based on a chemical property of the pharmaceutical composition 314 such as, for example, a solubility of the pharmaceutical composition 314.

Figure 6:
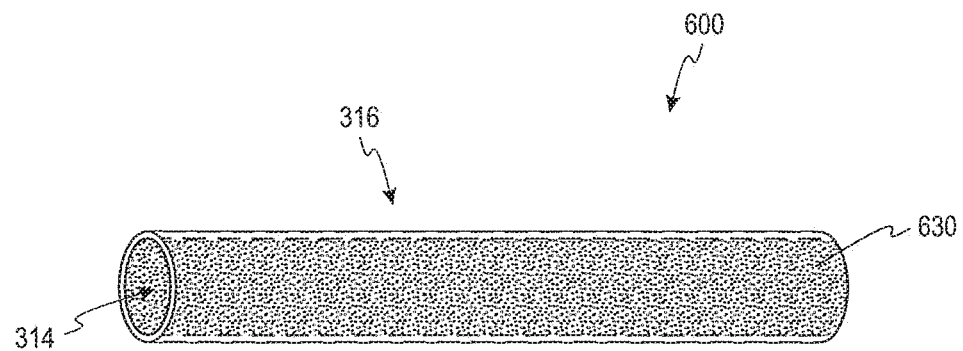
FIG. 6 shows a bioresorbable, nasal implant having a plurality of microspheres for drug delivery, according to an example.

In some examples, the bioresorbable implant 300, 400, 500 can additionally or alternatively include one or more bioresorbable microspheres. FIG. 6 shows a bioresorbable implant 600 that can be substantial similar or identical to the bioresorbable implants 300, 400, 500 of FIGS. 3-5, except the porous bioresorbable tube 316 of the bioresorbable implant 600 includes a plurality of bioresorbable microspheres 630 encapsulated therein. The microspheres 630 can be made of a polymer (e.g. PLGA) or a hydrogel and can include the pharmaceutical composition 314 therein. The microspheres 630 can advantageously have a large surface area that allows for increased and controlled release of the pharmaceutical composition 314.

In some examples, the microspheres 630 can additionally be suspended in a liquid form of the pharmaceutical composition 314 within the porous bioresorbable tube 316, thereby enabling a biphasic release. In some examples, the porous bioresorbable tube 316 of the bioresorbable implant 600 can be absorbable with or without apertures (e.g., the apertures 528) to tailor the delivery rate as well as implement a delay of initial release. In one specific example, the triamcinolone acetonide suspension used in Kenalog can be encapsulated in a dissolving excipient. Non-crosslinked hydrogels (e.g. PEG, HPMC) or crosslinked but biodegradable hydrogels (arterial gel paving chemistry) or biocompatible surfactants (e.g. Poloxamer family) can be used to encapsulate the pharmaceutical composition 314.

Figure 7:
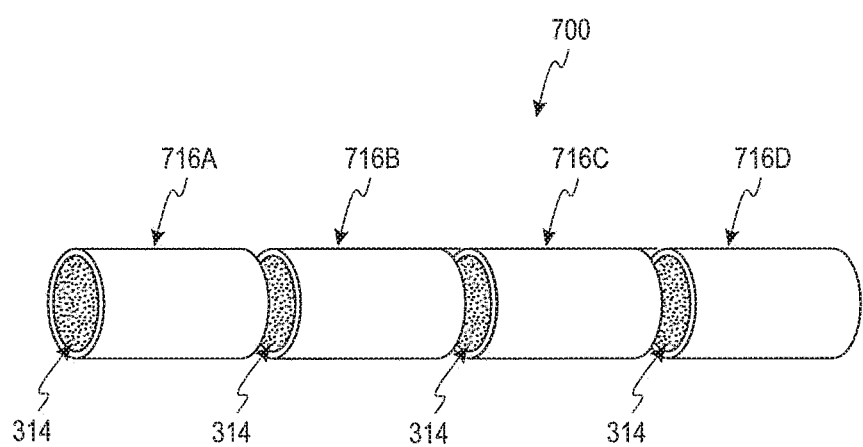
FIG. 7 shows a bioresorbable, nasal implant having a plurality of separate sections, according to an example.

In some examples, the bioresorbable implants 300, 400, 500, 600 can include a plurality of segments. For instance, as one example, FIG. 7 shows a bioresorbable implant 700 that include one or more short tubes 716A-716D (e.g., each having a length between 0.25 cm and 1 cm) that can be implanted separately or together. Each tube 716A-716D can be substantially similar or identical to the porous bioresorbable tube 316 described above, except each tube 716A-716D can have a relatively short length (i.e., in a dimension extending between the first end 320 and the second end 322). The short tubes 716A-716D can be used in combination with one another to adjust the dose of drug delivered. For example, each individual tube 716A-716D can include 5 mg of the pharmaceutical composition 314 therein (i.e., a total dosage of 20 mg for the combination of the four tubes 716A-716D in the example shown in FIG. 7). Delivering multiple small tubes 716A-716D can advantageously be used to control dose, and it can also enable distribution of the pharmaceutical composition 314 across different nasal tissues such as, for example, the inferior turbinate, the middle turbinate, the nasal septum, ethmoid cells, or polyp tissue.

Figure 8:
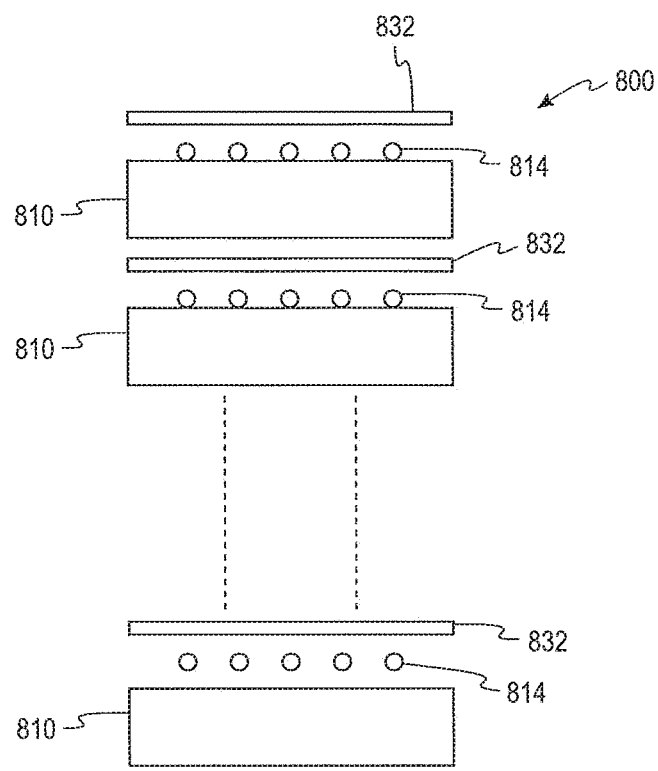
FIG. 8 shows an exemplary wall of a bioresorbable, nasal implant having multiple layers of drugs and coatings, according to an example.

Referring to FIG. 8, in some examples, a bioresorbable implant 800 is shown according to another example. The bioresorbable implant 800 includes one or more layers of a pharmaceutical composition 814, one more layers of parylene 832, and one or more layers of a polymeric bioresorbable substrate 810 arranged in stack. Stacking the layer(s) of the pharmaceutical composition 814, the layer(s) of the parylene 832, and the layer(s) of the polymeric bioresorbable substrate 810 can help to incorporate a relatively greater volume of the pharmaceutical composition 814 in a relatively small size and/or geometry (i.e., increase a density of the pharmaceutical composition 814).

In FIG. 8, the layer(s) of parylene 832 are arranged over the layer(s) of the pharmaceutical composition 814 and/or between the layer(s) of the pharmaceutical composition 814. The layer(s) of parylene 832 can help to control a release of the pharmaceutical composition 814 over a relatively long period of time. In an example, each layer parylene can have a thickness of approximately 0.1 microns to approximately 10 microns.

The layer(s) of the polymeric bioresorbable substrate 810 can include one or more of the polymeric materials described above with respect to the polymeric bioresorbable substrate 110 in FIG. 1. Within examples, the polymeric bioresorbable substrate 810 can provide a rigidity that facilitates insertion to the target tissue during implantation. In one example, the layer(s) of the polymeric bioresorbable substrate 810 can have a thickness that is less than approximately 1 mm.

Figure 9:
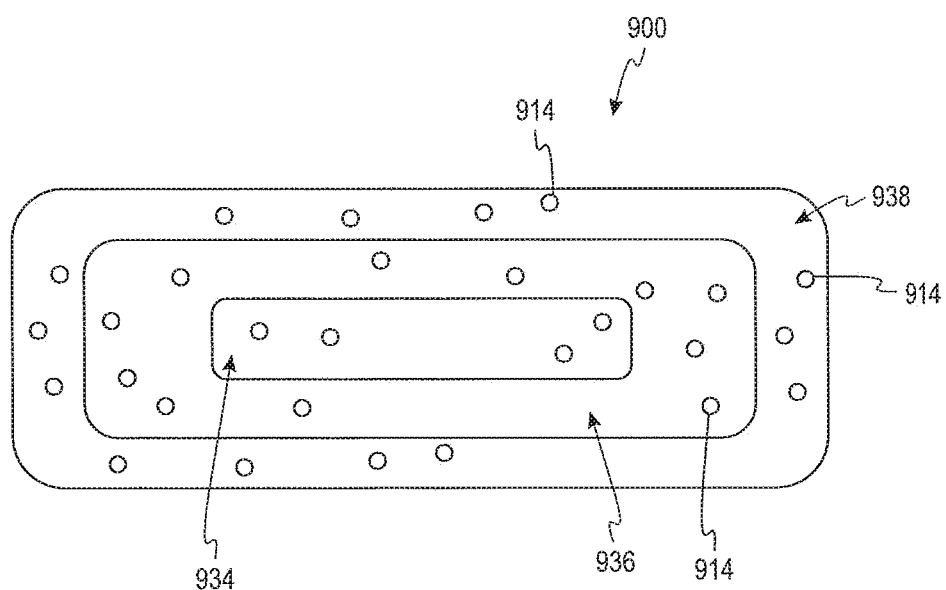
FIG. 9 shows a bioresorbable, nasal implant having multiple layers for timed drug delivery, according to an example.

FIG. 9 shows a bioresorbable implant 900 according to another example. As shown in FIG. 9, the bioresorbable implant 900 includes a plurality of layers 934, 936, 938 formed from a plurality of polymeric materials (such as the polymeric materials described above with respect to the polymeric bioresorbable substrate 110 in FIG. 1). Within examples, each layer 934, 936, 938 can include a different polymeric material in combination with a pharmaceutical composition 914. For instance, in FIG. 9, an inner layer 934 can include PCL and the pharmaceutical composition 914, a middle layer 936 can include PLA and the pharmaceutical composition 914, and an outer layer 938 can include PGA and the pharmaceutical composition 914.

By varying the type of polymeric material of each layer 934, 936, 938, a release rate of the pharmaceutical composition 914 can be controlled over a dosing time (e.g., over a time during which the bioresorbable implant 900 biodegrades and absorbs into a body of a patient). Within examples, the polymeric material of the outer layer 938 can have a first degradation rate, the polymeric material of the middle layer 936 can have a second degradation rate, and the polymeric material of the inner layer 934 can have a third degradation rate. In some implementations, the first degradation rate, the second degradation rate, and the third degradation rate can be different from each other. In other implementations, one or more of the first degradation rate, the second degradation rate, and/or the third degradation rate can be approximately equal to each other.

Also, in some examples, a concentration of the pharmaceutical composition 914 can be different for each layer 934, 936, 938. In one implementation, the degradation rates and the concentrations of the pharmaceutical composition 914 each be configured for each layer 934, 936, 938 such that the bioresorbable implant 900 provides a relatively constant dosage of the pharmaceutical composition 914 over a lifespan of the bioresorbable implant 900. This can include configuring the polymeric materials and/or the concentrations of each layer 934, 936, 938 to account for a constantly reducing surface area of the bioresorbable implant 900 as the layers 934, 936, 938 biodegrade.

Figure 10:
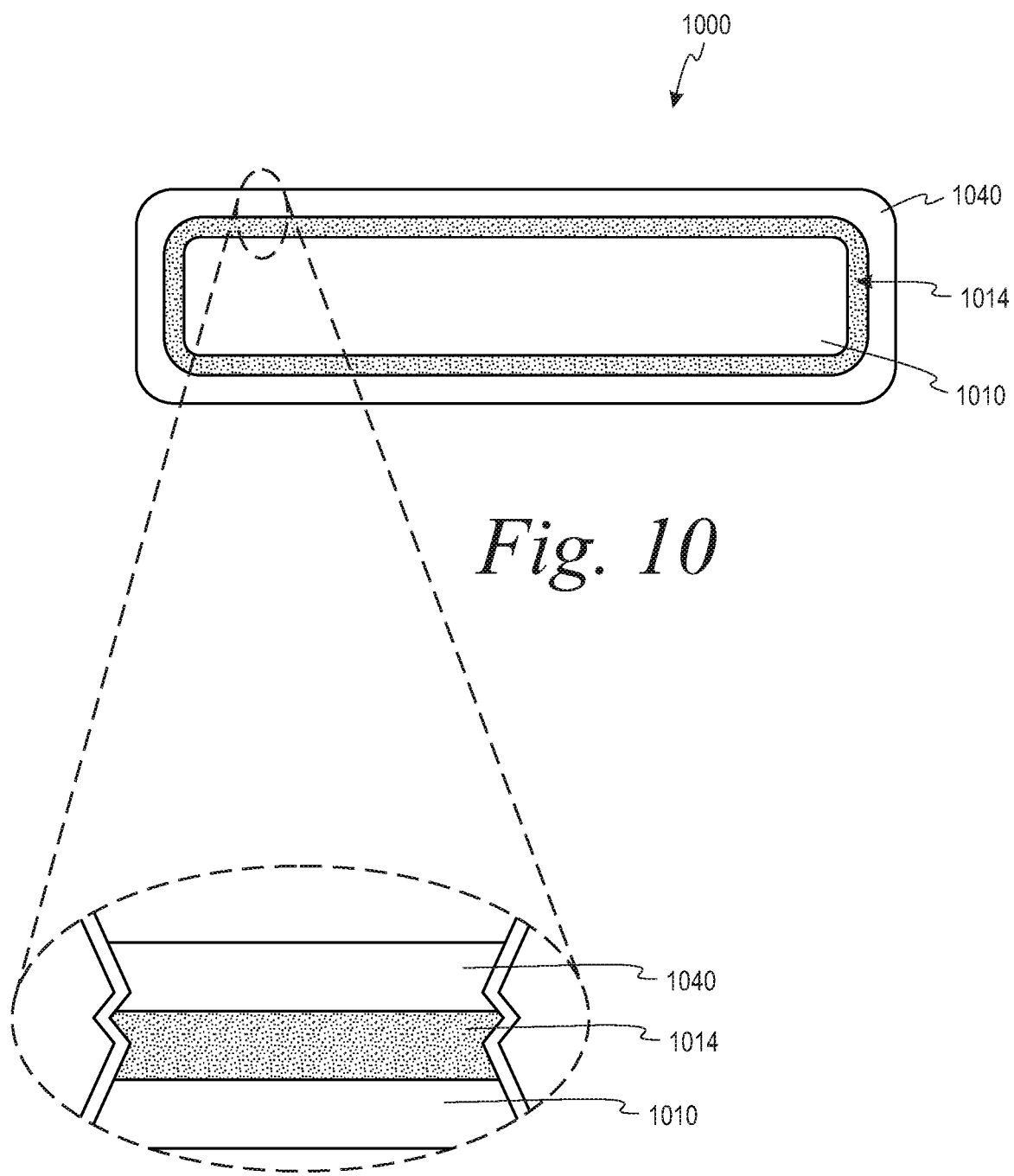
FIG. 10 shows a nasal implant including a substrate, a drug layer, and an outer release controlling layer, according to an example.

FIG. 10 shows a bioresorbable implant 1000 according to another example. The bioresorbable implant 1000 includes a polymeric bioresorbable substrate 1010, a layer of a pharmaceutical composition 1014, and a release-control layer 1040. As shown in FIG. 10, the polymeric bioresorbable substrate 1010 is an inner layer, the layer of the pharmaceutical composition 1014 is a middle layer on an outer surface of the polymeric bioresorbable substrate 1010, and the release-control layer 1040 is an outer layer on an outer surface of the layer of the pharmaceutical composition 1014. In an example, the layer of the pharmaceutical composition 1014 can completely enclose the polymeric bioresorbable substrate 1010, and the release-control layer 1040 can completely enclose the layer of the pharmaceutical composition 1014.

In general, the polymeric bioresorbable substrate 1010 can be made from a polymer material that is bioresorbable and provides rigidity to facilitate inserting the bioresorbable implant 1000 to an implantation site in a patient and/or retaining the bioresorbable implant 1000 at the implantation site. For instance, the polymeric bioresorbable substrate 1010 can be made from one or more of the example polymers described herein with respect to the polymeric bioresorbable substrate 110 of FIG. 1.

In some examples, the layer of the pharmaceutical composition 1014 can be a bioresorbable polymeric coating (e.g., the coating 112 described above) having a coating matrix for retaining the pharmaceutical composition 1014 prior to release. In other examples, the layer of the pharmaceutical composition 1014 can be a different type of coating or covering so long as the layer of pharmaceutical composition 1014 is bioresorbable.

Within examples, the release-control layer 1040 can be configured to control a release rate of the pharmaceutical composition 1014. For instance, the release rate of the pharmaceutical composition 1014 can be additionally based on a degradation rate of the release-control layer 1040, a degradation rate of the bioresorbable polymeric coating containing the pharmaceutical composition 1014, and/or a solubility of the pharmaceutical composition 1014.

In some implementations, the polymeric bioresorbable substrate 1010 can be a solid or hollow cylindrical bioresorbable matrix (e.g., PLLA/PDLLA copolymers, PLA/PGA copolymers, PLA/PCL copolymers, PGLA, PLLA, etc.), which can be covered/coated with a layer of the pharmaceutical composition 1014 having a defined thickness (e.g. mometasone furoate), which is then covered by the release-control layer 1040. Within examples, the release rate of the pharmaceutical composition 1014 can be based, at least in part, on a thickness of the release-control layer 1040 and a thickness of the layer of the pharmaceutical composition 1014. The release-control layer 1040 can be made from another material or the same material (e.g. PDLA) relative to the layer of the pharmaceutical composition 1014 to control the release rate.

Figure 11:
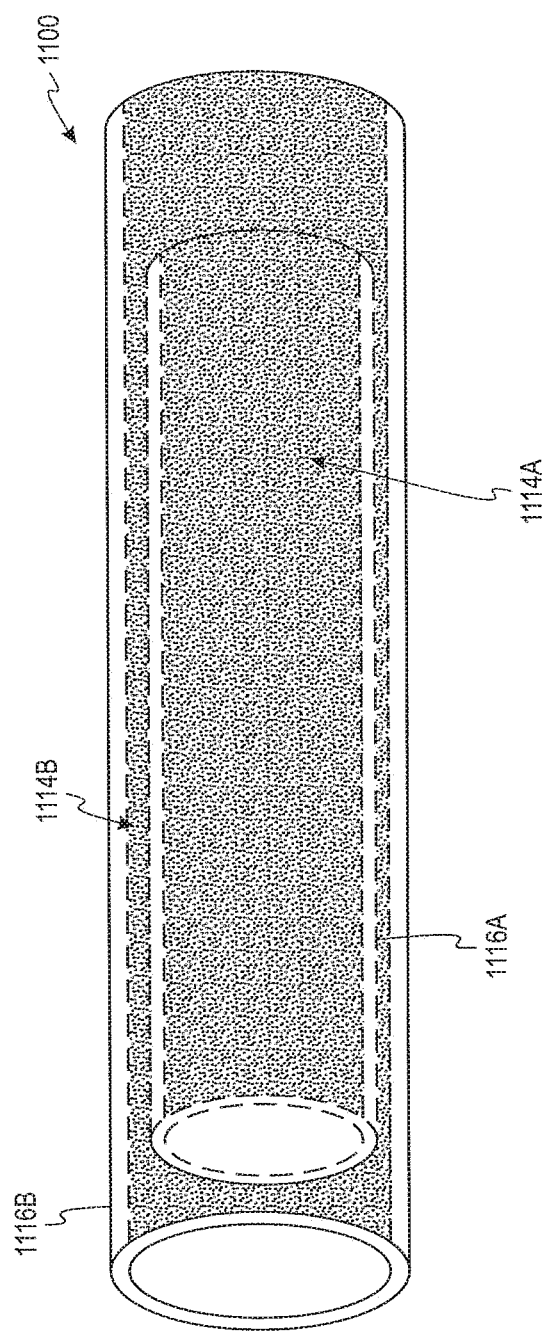
FIG. 11 shows a bioresorbable, nasal implant having a plurality of tubes in a nested arrangement, according to an example.

In some of the examples described above, the bioresorbable implants 300, 400, 500, 600, 700, 900, 1000 can include a tube (e.g., the polymeric bioresorbable tube 316) in which the pharmaceutical composition 314, 914, 1014 is located. In other examples, a bioresorbable implant can include a plurality of bioresorbable tubes in a nested arrangement with each other. As an example, FIG. 11 shows a bioresorbable implant 1100 including a first bioresorbable tube 1116A filled with a first pharmaceutical composition 1114A that is encapsulated in a second, larger bioresorbable tube 1116B which is filled with a second pharmaceutical composition 1114B. The second pharmaceutical composition 1114B can be the same or different than the first pharmaceutical composition 1114A. This can enable the second bioresorbable tube 1116B to release the second pharmaceutical composition 1114B at a first rate, followed by the first bioresorbable tube 1116A releasing the first pharmaceutical composition 1114A at a second rate. Based on the selected bioresorbable tubes 1116A-1116B, the bioresorbable implant 1100 can provide for an overlap of delivery of the first pharmaceutical composition 1114A and the second pharmaceutical composition 1114B or, alternatively, the bioresorbable implant 1100 can be configured with a time delay between completion of elution of the second pharmaceutical composition 1114B and an onset of a release of the first pharmaceutical composition 1114A.

Although often described herein as being used with a corticosteroid, it should be understood that the bioresorbable implants 100, 200, 300, 400, 500, 600, 700, 800, 900, 1000, 1100 described herein can be used to deliver other drugs or therapeutic agents as well. For example, the bioresorbable implants 100, 200, 300, 400, 500, 600, 700, 800, 900, 1000, 1100 can be used with an antibiotic, a chemotactic agent, a nerve denervation agent, or a vasoconstricting agent. In some implementations, the bioresorbable implants 100, 200, 300, 400, 500, 600, 700, 800, 900, 1000, 1100 can be configured to include anti-inflammatory agents, tissue growth factors, or chemotactic agents. Additionally, the bioresorbable implants 100, 200, 300, 400, 500, 600, 700, 800, 900, 1000, 1100 can be used to treat disease states other than (or in addition to) allergic rhinitis, such as infectious diseases, osteoporosis, migraine headaches, and/or cluster headaches.

In any of the examples described herein, the bioresorbable implant 100, 200, 300, 400, 500, 600, 700, 800, 900, 1000, 1100 can include features to prevent the bioresorbable implant 100, 200, 300, 400, 500, 600, 700, 800, 900, 1000, 1100 from migrating once implanted. Specifically, the bioresorbable implant 100, 200, 300, 400, 500, 600, 700, 800, 900, 1000, 1100 can include one or more retention features such as barbs, hooks, and/or forks that inhibit (or prevent) migration of the bioresorbable implant 100, 200, 300, 400, 500, 600, 700, 800, 900, 1000, 1100 out of a tissue channel made during delivery and/or that inhibit (or prevent) movement of the bioresorbable implant 100, 200, 300, 400, 500, 600, 700, 800, 900, 1000, 1100 in other directions.

In the examples described above, the bioresorbable implants 100, 200, 300, 400, 500, 600, 700, 800, 900, 1000, 1100 can be entirely bioresorbable. In other examples, one or more portions of the bioresorbable implants 100, 200, 300, 400, 500, 600, 700, 800, 900, 1000, 1100 can be a non-bioresorbable material. For instance, in one implementation, the tubes and/or the rods of the bioresorbable implant 100, 200, 300, 400, 500, 600, 700, 800, 900, 1000, 1100 can be made of a durable material that is not absorbed into the body rather than of an absorbable material. Some example polymeric materials that are not bioresorbable include polyimide, nylon, pebax, polyurethane, polyethylene terephthalate, polyethylene, PEEK, silicone and polypropylene. Other example materials that are not bioresorbable include stainless steel, titanium and nickel titanium. In such an example, the controlled release can be achieved by either micro holes along the length of the tube or via a permeable membrane, or porous end cap on either or both ends of the tube.

In any of the examples described herein, the bioresorbable implants 100, 200, 300, 400, 500, 600, 700, 800, 900, 1000, 1100 can be made of hollow tubes where the ends are capped by thermally welding or solvent bonding on end caps of similar materials. In some examples, if the tube is nonresorbable, the end caps can be bioresorbable of thickness and composition selected to control the drug elution rate and/or the ends can be thermally swaged closed.

Any of the implants that are not bioresorbable described herein can be covered with a release controlling layer of bioresorbable or non-bioresorbable material of defined thickness (e.g. PLLA/PDLLA copolymer, PLA/PGA copolymer, PGA, PVA, Parylene, etc.).

Any of the implants that are not bioresorbable described herein can be designed to have a biphasic release profile, as described above with respect to some examples. A percentage of drug in the polymer will affect the release rate. A magnitude of the initial burst of drug can be beneficially used to have a more rapid onset of symptom relief. This biphasic release of the inventive implants may have therapeutic effects similar to the Kenalog intraturbinal injection with its rapid relief, and sustained relief due to the linear release phase that is more similar to that offered by nasal sprays with daily administration. Thus, the drug release rate features may be implemented in combination to achieve the biphasic release profile. Examples include implementing both permeable end caps as well as micro holes, implementing two or more chambers with different quantity or size holes in each chamber for drug release. Additional biphasic release examples described below.

The drug dose and release rate from the implants described herein can vary based on the intended treatment effect. For example, a high dose delivered over a short period of time can be similar to the intraturbinal Kenalog-40 injection. This has been shown to be highly efficacious for severe symptoms, and the effect lasts about 3-6 weeks. For example, a lower sustained release can be similar to nasal sprays. Over a period of 6 weeks, the total dose from a nasal spray is 8.4 mg, but most of this is swallowed or rapidly cleared by mucociliary action and does not directly contribute to the efficacy. The total nasal spray dose over a period of 6 months is 36.5 mg, but the large percentage of this dose that is swallowed is subsequently metabolized and therefore does not contribute to the therapeutic effect. Thus, the nasal implants described herein can mimic these traditional dosing regimens and/or provide optimized profiles. For example, an implant as described herein can deliver a relatively constant daily drug dose comparable to a nasal spray. Since most of the drug is swallowed, the daily drug dose from the implant may only need to be 10%-50% of that administered by a nasal spray. In some examples, the implant can be configured to deliver a high dose of drug over a few days to weeks, which may be more efficacious in severe cases. Additionally, in some examples, an implant can combine a higher initial release rate to treat more severe symptoms with a sustained daily dose to prevent recurrence. A first order release may have a similar clinical effect to this high initial release rate combined with a lower sustained release rate. Since the implants described herein can be delivered into each side of the nasal passages, the drug dose in each side can be only half of the total daily dose delivered to the patient. The release rate for the implants described herein can be on the order of days to weeks, but may be longer (e.g., months or years) using less water-soluble steroids.

Figure 12:
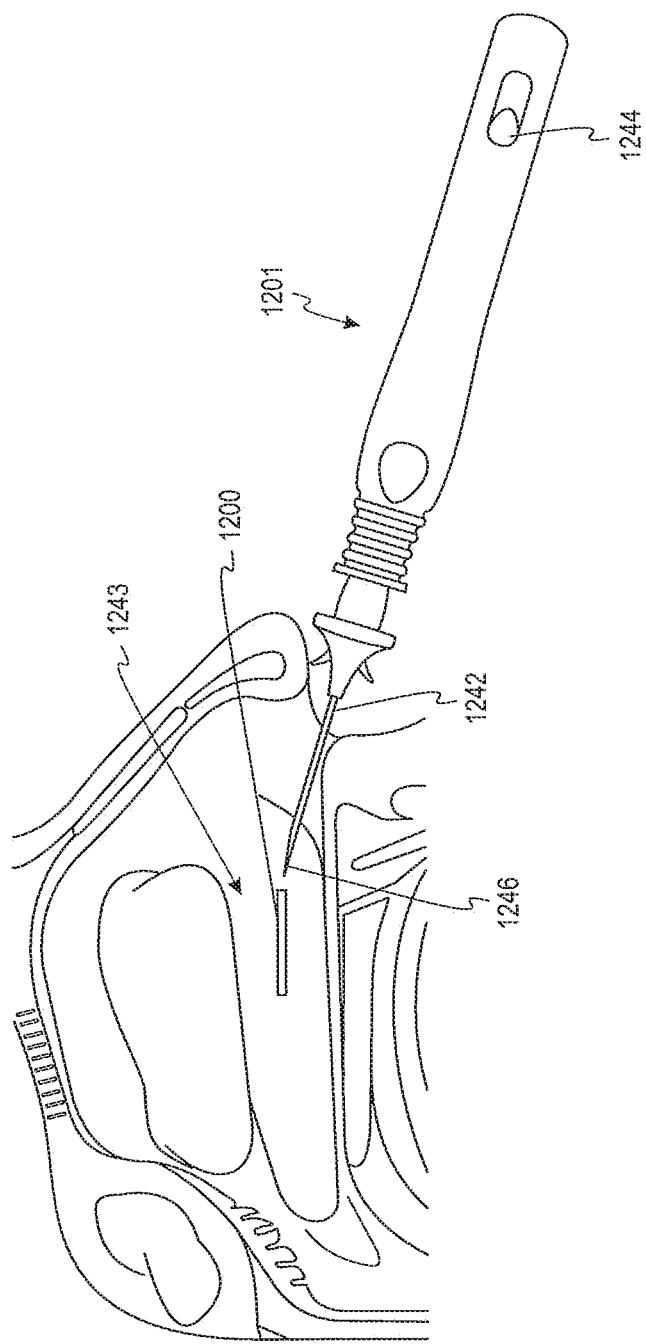
FIG. 12 shows a system including a bioresorbable implant and a delivery device, according to an example.

As described above, the bioresorbable implants 100, 200, 300, 400, 500, 600, 700, 800, 900, 1000, 1100 described herein can be delivered using a needle injection delivery system. Exemplary delivery systems are described in International Application No. PCT/US2016/53480, filed Sep. 23, 2016, the entirety of which is incorporated by reference herein. Additionally, FIG. 12 shows a delivery device 1201 according to an example. As shown in FIG. 12, the delivery device 1201 can include a needle 1242 that defines a lumen extending through the needle 1242. The needle 1242 can be configured to be inserted in a tissue 1243 to access an implantation site. Within examples, a bioresorbable implant 1200 (e.g., the bioresorbable implants 100, 200, 300, 400, 500, 600, 700, 800, 900, 1000, 1100) can be inserted to the implantation site via the lumen of the needle 1242. For instance, the delivery device 1201 can include an actuator 1244 that can cause the bioresorbable implant 1200 to move along the needle 1242 and exit the lumen of the needle 1242 at a pointed tip 1246 of the needle 1242.

Advantageously, the bioresorbable implants 100, 200, 300, 400, 500, 600, 700, 800, 900, 1000, 1100, 1200 described herein allow for a very simple needle injection, for example into a turbinate (e.g., the superior, middle, or inferior turbinates). A portion of a dose of a pharmaceutical composition can be delivered into other parts of the nasal region such as into the mucosa overlying the septum, the muscosal surfaces of the middle meatus or the ethmoid bulla, any tissue/cell location of the nasal osteomeatal complex, or any other portion of the nasal anatomy that has a layer of mucosal tissue thick enough to contain or cover the implant.

In some examples, the bioresorbable implant 100, 200, 300, 400, 500, 600, 700, 800, 900, 1000, 1100, 1200 can translate from an implant carrying cartridge of the delivery device (e.g., the delivery device 1201) through the needle injection portion and to the intended implantation site without being disposed within the needle prior to or during the implantation step.

Figure 13A:
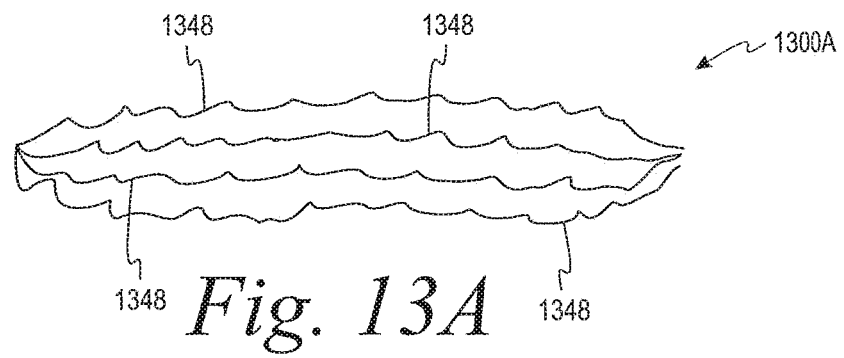
FIG. 13A shows a fibrous/bulking turbinate stiffening nasal implant, according to an example.
Figure 13B:
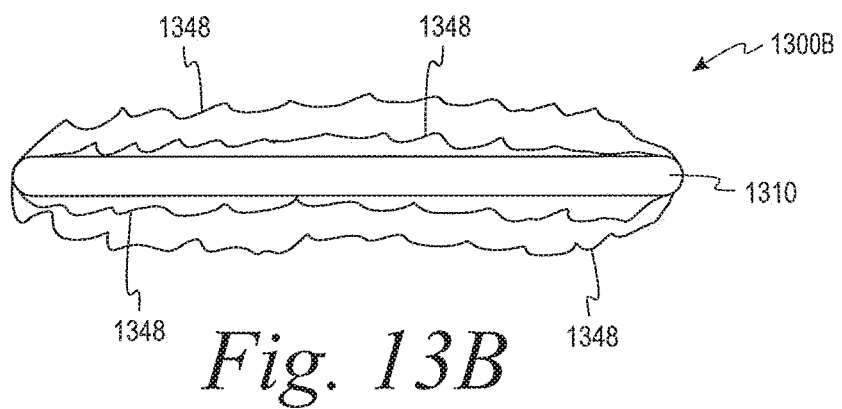
FIG. 13B shows a fibrous/bulking turbinate stiffening nasal implant, according to another example.

Referring to FIGS. 13A and 13B, in some examples, a bioresorbable implant 1300A, 1300B can be made from bioresorbable textile fibers 1348 (which can be bioresorbable drug eluting textile fibers) useful for bulking or stiffening nasal tissue including nasal turbinate tissue. The textile fibers 1348 can be randomly arranged, knitted or non-knitted, woven or non-woven, and range in size from 0.1 denier to 20 denier or more. Within examples, the bioresorbable implant 1300A, 1300B can include between 100 and 200,000 textile fibers 1348.

As shown in FIG. 13A, the bioresorbable implant 1300A can be made substantially of the textile fibers 1348, which can be made from the materials described herein and can releasably retain the pharmaceutical composition described herein. In some implementations, the textile fibers 1348 can be coupled at respective end portions of the textile fibers 1348. In other implementations, the end portions of the textile fibers 1348 are not coupled to each other.

In FIG. 13B, the bioresorbable implant 1300B includes a bioresorbable substrate 1310 (e.g., a rod, tube, or solid drug delivery section) surrounded by the textile fibers 1348. In this example, a primary pharmaceutical composition payload can be part of the bioresorbable substrate 1310, and the textile fibers 1348 can provide additional bulking features to the bioresorbable implant 1300B. Also, in this example, the textile fibers 1348 can be with or without the pharmaceutical composition.

Figure 14:
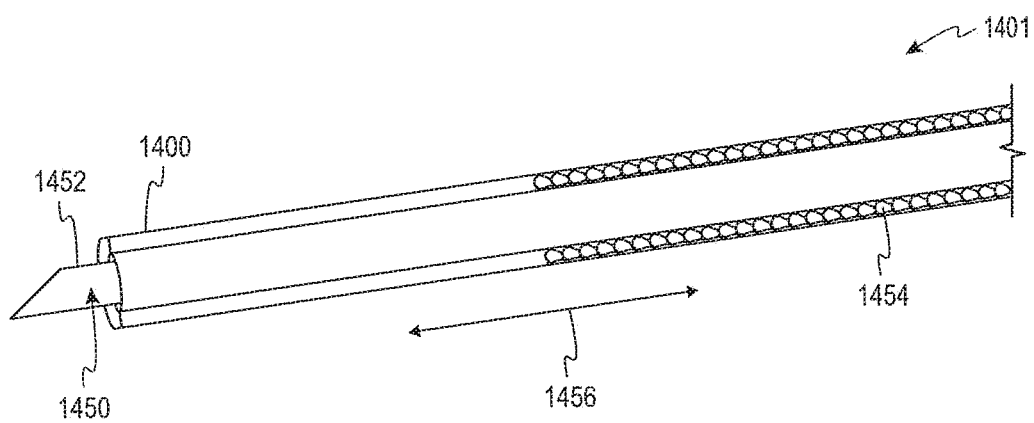
FIG. 14 shows tubular implant on periphery of fixed carrying needle or trocar for delivery, according to an example.

Referring to now FIG. 14, a delivery device 1401 is shown according to another example. In FIG. 14, the delivery device 1401 includes an elongated shaft 1450 that is configured to be inserted in tissue to access an implantation site. As examples, the elongated shaft 1450 can include a needle, a trocar, a rod, and/or a cannula. The elongated shaft 1450 is configured to carry a bioresorbable implant 1400 (e.g., the bioresorbable implant 300, 400, 500, 600, 700, 1100) on an exterior surface 1452 of the elongated shaft 1450. For instance, the elongated shaft 1450 can have a cross-sectional shape and/or size that is smaller than a cross-sectional shape and/or size of an interior bore 1424 of the bioresorbable implant 1400.

Within examples, the elongated shaft 1450 can be configured to axially retain the bioresorbable implant 1400 in a pre-delivery position by a frictional fit. As shown in FIG. 14, the delivery device 1401 can further include a second outer member 1454 that is translatable along an axial direction 1456 of the elongated shaft 1450 (i.e., in a direction parallel to a longitudinal axis of the elongated shaft 1450) to push the bioresorbable implant 1400 off the elongated shaft 1450 into the nasal tissue at the implantation site.

As described above, in some examples, the bioresorbable implants 100, 200, 300, 400, 500, 600, 700, 800, 900, 1000, 1100, 1200, 1300, 1400 can be delivered to an implantation site using a delivery device (e.g., the delivery devices 1201, 1401) that includes a pointed tip for piercing and penetrating tissue to access the implantation site. However, in other examples, the bioresorbable implants can additionally or alternatively include one or more penetration features allowing for self-tissue piercing and penetration (and, thus, allow a bioresorbable implant to act as a delivery needle). As examples, FIGS. 15-20 show bioresorbable implants that include a tip having a pointed shape (e.g., a sharp shape) to facilitate piercing and penetrating the tissue and delivering the bioresorbable implants to the implantation site.

Figure 15:
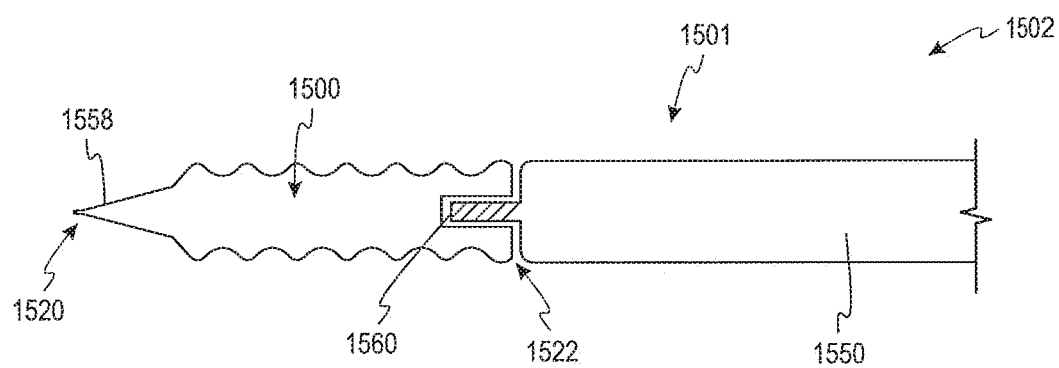
FIG. 15 shows a bioresorbable, nasal implant having features for tissue penetration, according to an example.

FIG. 15 shows a system 1502 that includes a bioresorbable implant 1500 having a distal end 1520 and a proximal end 1522. The distal end 1520 includes a tip 1558 with a pointed shape configured to pierce and penetrate tissue. The proximal end 1522 can be configured to couple to a delivery device 1501 of the system 1502. The bioresorbable implant 1500 can otherwise be substantially similar or identical to the bioresorbable implants 100, 200, 300, 400, 500, 600, 700, 800, 900, 1000, 1100, 1200, 1300, 1400 described above.

As shown in FIG. 15, the delivery device 1501 includes an elongated shaft 1550. The elongated shaft 1550 is releasably coupled to the proximal end 1522 of the bioresorbable implant 1500. In this way, the delivery device 1501 can carry the bioresorbable implant 1500 at a distal end 1560 of the elongated shaft 1550 (e.g., delivery rod or tube) and can be inserted into the nasal tissue using the tip 1558 (i.e., the self-piercing feature) of the bioresorbable implant 1500.

In this example, the delivery device 1501 can release the bioresorbable implant 1500 responsive to rotation of the elongated shaft 1550 relative to the bioresorbable implant 1500. For example, in FIG. 15, the proximal end 1522 of the bioresorbable implant 1500 and the distal end 1560 of the elongated shaft 1550 can include respective threads that can threadedly couple the bioresorbable implant 1500 and the delivery device 1501. In this arrangement, after penetrating the issue and inserting the bioresorbable implant 1500 to the implantation site, the elongated shaft 1550 can be rotated relative to the bioresorbable implant 1500 to unscrew the delivery device 1501 from the bioresorbable implant 1500. In some implementations, the bioresorbable implant 1500 can remain substantially rotationally fixed relative to the tissue at the implantation site (e.g., due to friction).

Figure 16:
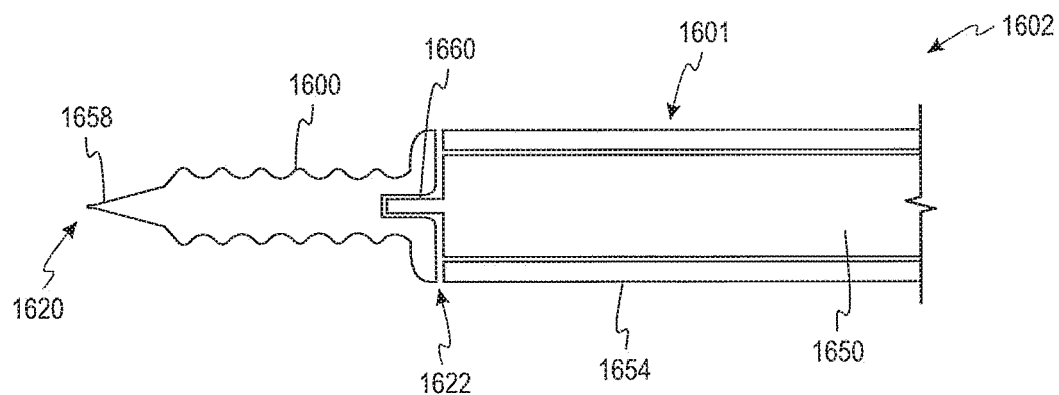
FIG. 16 shows a bioresorbable, nasal implant having features for tissue penetration, according to another example.

FIG. 16 shows a system 1602 that includes a bioresorbable implant 1600 having a distal end 1620 and a proximal end 1622. The distal end 1620 includes a tip 1658 with a pointed shape configured to pierce and penetrate tissue. The proximal end 1622 can be configured to couple to a delivery device 1601 of the system 1602. The bioresorbable implant 1600 can otherwise be substantially similar or identical to the bioresorbable implants 100, 200, 300, 400, 500, 600, 700, 800, 900, 1000, 1100, 1200, 1300, 1400 described above.

As shown in FIG. 16, the delivery device 1601 includes an elongated shaft 1650. The elongated shaft 1650 is releasably coupled to the proximal end 1622 of the bioresorbable implant 1600. In this way, the delivery device 1601 can carry the bioresorbable implant 1600 at a distal end 1660 of the elongated shaft 1650 (e.g., delivery rod or tube) and can be inserted into the nasal tissue using the tip 1658 (i.e., the self-piercing feature) of the bioresorbable implant 1600.

In this example, the proximal end 1622 of the bioresorbable implant 1600 can be coupled to the distal end 1660 of the elongated shaft 1650 by a friction fit (i.e., without threads). As shown in FIG. 16, the delivery device 1601 can further include a push member 1654 that is translatable along a dimension parallel to a longitudinal axis of the elongated shaft 1650. Specifically, the push member 1654 can be translated distally toward the bioresorbable implant 1600 to push the bioresorbable implant 1600 away from the distal end 1660 of the elongated shaft and thereby decouple the bioresorbable implant 1600 from the delivery device 1601. In this arrangement, after penetrating the issue and inserting the bioresorbable implant 1600 to the implantation site, the push member 1654 can be translated along the elongated shaft 1650 to push the bioresorbable implant 1600 off of the delivery device 1601.

Figure 17:
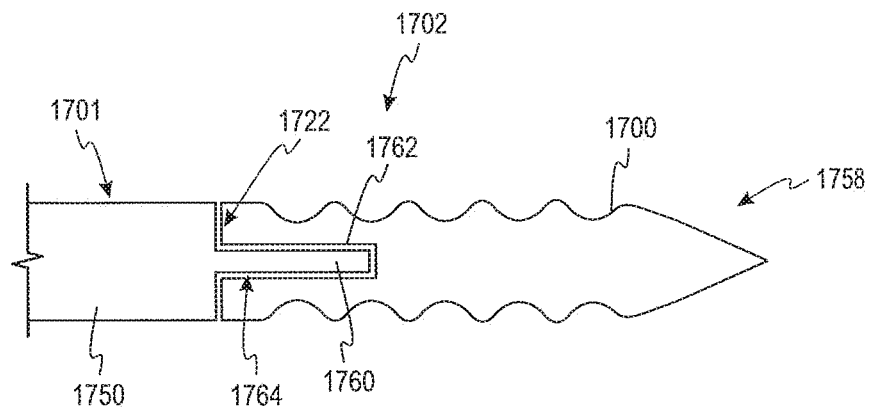
FIG. 17 shows a bioresorbable, nasal implant having features for tissue penetration, according to another example.

FIG. 17 shows a system 1702 that includes a bioresorbable implant 1700 and a delivery device 1701, according to another example. The bioresorbable implant 1700 and the delivery device 1701 are substantially similar or identical to the bioresorbable implant 1600 and the delivery device 1601 of FIG. 16, except the bioresorbable implant 1700 and the delivery device 1701 are configured to be coupled to each other in a looser manner.

Specifically, a proximal end 1722 of the bioresorbable implant 1700 can include a recess 1762 that is configured to receive a distal end 1760 of an elongated shaft 1750 of the delivery device 1701 such that a gap 1764 is formed (i) at least partially around a circumference of the recess 1762 and (ii) between the recess 1762 and the distal end 1760 of the elongated shaft 1750. In this way, the distal end 1760 does not couple to the recess 1762 by a friction fit. In this arrangement, the bioresorbable implant 1700 can be loosely coupled to the delivery device 1701 so as to be pushed into the target tissue via a tip 1758 (e.g., under direct visualization) and, upon retraction of the delivery device 1701, the bioresorbable implant 1700 can release and stay embedded in the tissue.

Figure 18:
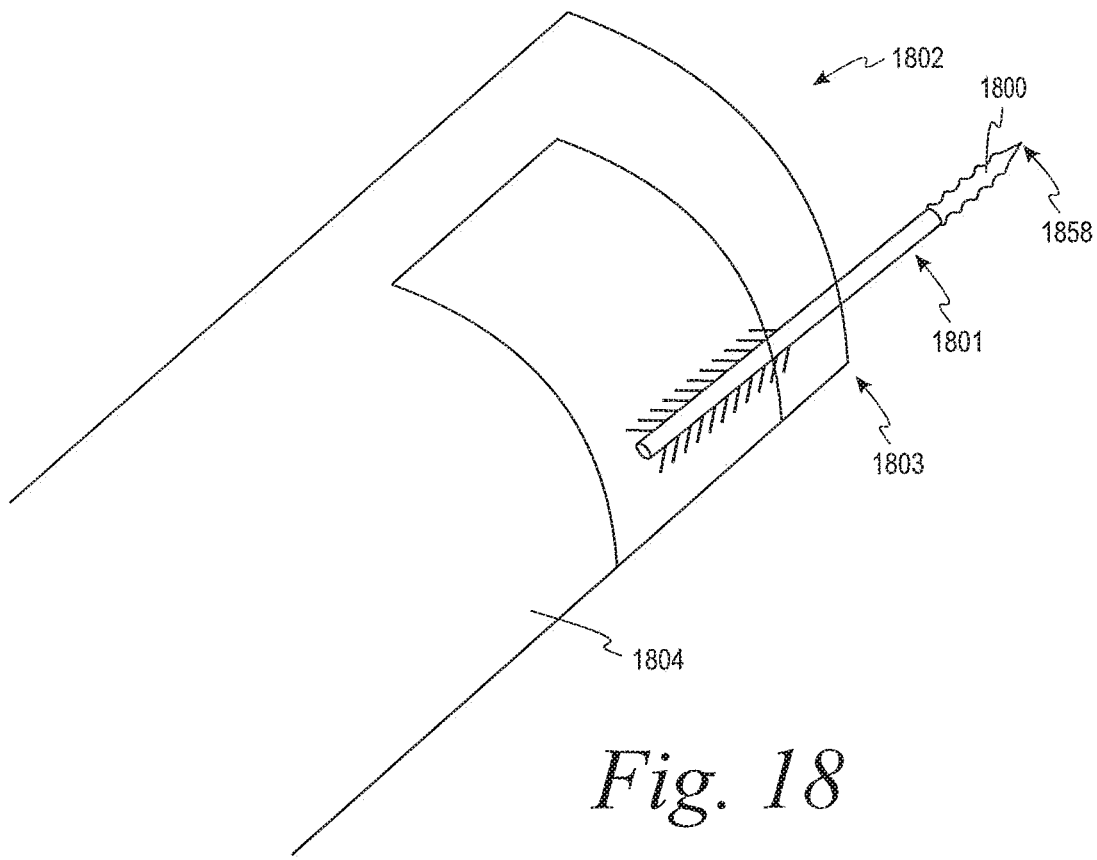
FIG. 18 shows a bioresorbable, nasal implant having features for tissue penetration, according to another example.

FIG. 18 shows a system 1802 that includes a bioresorbable implant 1800 and a delivery device 1801, according to another example. As shown in FIG. 18, the bioresorbable implant 1800 can be maneuvered into position by the delivery device 1801 that is attached to a distal end 1803 of a scope 1804, such as an endoscope. The bioresorbable implant 1800 can include a tip 1858 having a pointed shape, as described above.

In FIGS. 15-18, the bioresorbable implant 1500, 1600, 1700, 1800 includes a recess (e.g., the recess 1762) at the proximal end 1522, 1622, 1722 that receives the distal end 1660, 1760 of the elongated shaft 1550, 1652, 1752, 1852 to couple the bioresorbable implant 1500, 1600, 1700, 1800 to the delivery device 1501, 1601, 1701, 1801. However, in other examples, the distal end of 1660, 1760 of the elongated shaft 1550, 1562, 1752, 1852 can include a recess and the bioresorbable implant 1500, 1600, 1700, 1800 can include a protrusion that is received in the recess of the elongated shaft 1550, 1652, 1752, 1852.

Figure 19:
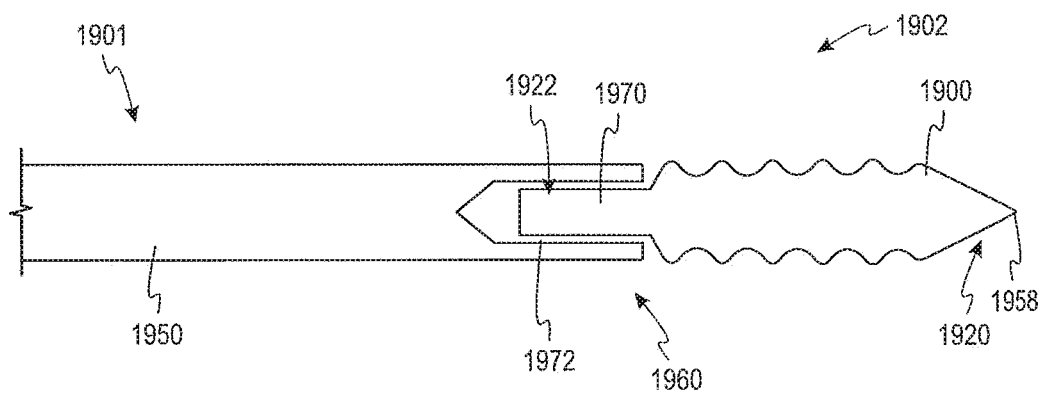
FIG. 19 shows a bioresorbable, nasal implant having features for tissue penetration, according to another example.

FIG. 19 shows a system 1902 including a bioresorbable implant 1900 and a delivery device 1901 according to another example. As shown in FIG. 19, the bioresorbable implant 1900 includes a protrusion 1970 at a proximal end 1922 and a tip 1958 at a distal end 1920. Also, as shown in FIG. 19, the delivery device 1901 includes an elongated shaft 1950 having a recess 1972 at a distal end 1960 of the elongated shaft 1950. In this arrangement, the protrusion 1970 of the bioresorbable implant 1900 can be coupled to the recess 1972 (e.g., via a threaded coupling, a friction fit coupling, a relatively loose non-friction fit coupling, and/or a clip).

Figure 20:
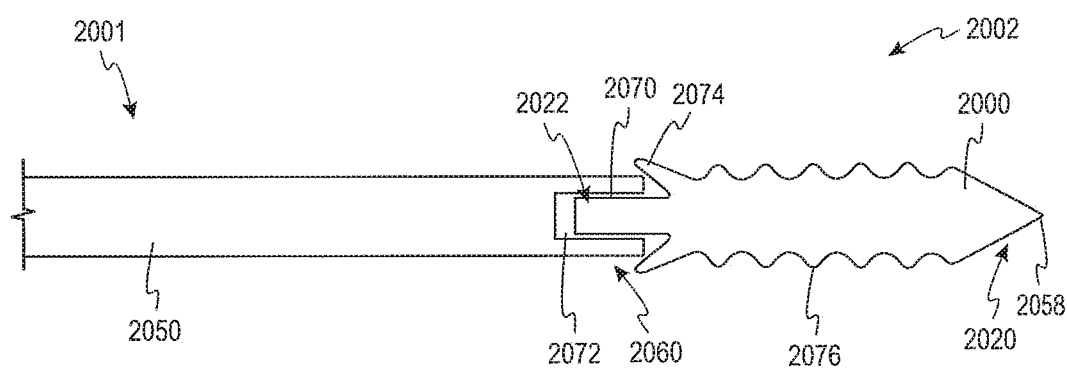
FIG. 20 shows a bioresorbable, nasal implant having features for tissue penetration, according to another example.

FIG. 20 shows a system 2002 including a bioresorbable implant 2000 and a delivery device 2001 according to another example. As shown in FIG. 20, the bioresorbable implant 2000 includes a protrusion 2070 at a proximal end 2022 and a tip 2058 at a distal end 2020. Also, as shown in FIG. 20, the delivery device 2001 includes an elongated shaft 2050 having a recess 2072 at a distal end 2060 of the elongated shaft 2050. In this arrangement, the protrusion 2070 of the bioresorbable implant 2000 can be coupled to the recess 2072 (e.g., via a threaded coupling, a friction fit coupling, a relatively loose non-friction fit coupling, and/or a clip).

Additionally, in FIG. 20, the bioresorbable implant 2000 includes a plurality of retention barbs 2074. The retention barbs 2074 are configured to assist in retaining the bioresorbable implant 2000 at an implantation site in a tissue. For example, the retention barbs 2074 can extend proximally and outwardly from an exterior surface 2076 of the bioresorbable implant 2000. As such, when the bioresorbable implant 2000 is implanted at the implantation site, the retention barbs 2074 can engage the tissue to help maintain a position of the bioresorbable implant 2000 in the tissue (e.g., mitigating the bioresorbable implant 2000 migrating out of a pathway in the tissue formed during implantation).

Within examples, the retention barbs 2074 can additionally or alternatively assist in releasing the bioresorbable implant 2000 from the elongated shaft 2050 of the delivery device 2001. For instance, the retention barbs 2074 can extend outwardly beyond an outer circumference of the elongated shaft 2050. In this arrangement, when the elongated shaft 2050 is pulled proximally away from the bioresorbable implant 2000, the retention barbs 2074 can catch on the tissue at the implantation site and thereby facilitate decoupling the bioresorbable implant 2000 from the elongated shaft 2050.

Within examples, any of the bioresorbable implants 1500, 1600, 1700, 1800, 1900, 2000 having a tip 1558, 1658, 1758, 1858, 1958, 2058, which is self-piercing (e.g., having a tip with a pointed shape) described herein can be clipped or otherwise attached to the tip of a standard nasal endoscope to facilitate more accurate placement or placement deeper into the nasal cavity (e.g., as shown in FIG. 18).

Any of the examples described herein can also be used for additional tissue stiffening properties to effect nasal airway obstruction and improve airflow. As described herein, the therapeutic agent can be selected to improve the fibrotic or scar tissue healing response in order to create more bulk and stiffness within the tissue. For example, in the case of bioresorbable examples, during the acute degradation phase, the implant structure and therapeutic agent can contribute to the tissue stiffening properties. During degradation and post-degradation the therapeutic agent delivered can contribute primarily to the tissue stiffening properties.

The mechanisms by which fibrotic healing can occur include, but are not limited to, formation of an organized fibrotic reaction resulting from the body's natural foreign body healing response, formation of a wound or damage to tissue, expansion of the implant device or material, release of a chemical or bioactive agent (e.g., cellular inflammatory agent, cytokine, growth factor, clotting factor, tissue attachment factor, or other agent) from the implant device or material. Other mechanisms, forms, and effects of fibrotic healing will be appreciated by those of skill in the art.

In some examples, for example in tissue bulking or stiffening, bioactive agents that illicit the tissue healing response and promote a more durable foreign body response and fibrotic healing may be used. For example, in some examples, the implant may be pre-treated with desirable therapeutic and clinical agents such as growth factors, tissue attachment factors, clotting factors, chemotherapeutic agents, chemotactic factors, and anti-bacterial agents. These agents may be covalently bonded, ionically or hydrophobically bonded, coated, compounded, physically absorbed into the implant, or otherwise combined with the implant. Some bioactive agents include but are not limited to: antibiotics such as tobramycin, entamycin, and vancomycin; clotting factors such as Factors I-VIII, thrombin, and fibrinogen; cytokines for example basic fibroblast growth factor (bFGF), platelet derived growth factor (PDGF), vascular endothelial growth factor (VEGF), transforming growth factor beta (TGF-.beta.), TNF.alpha., NGF, GM-CSF, IGF.alpha., IL-1, IL-8, and IL-6; inflammatory microcrystals such as crystalline minerals and silicates; tissue attachment factors such as fibronectin, laminin, and vitronectin; protease inhibitors such aprotinin; extracellular matrix molecules such as collagen and fibronectin; trace metals; irritants such as trace amounts of talcum powder, metallic beryllium and silica; trace amounts of polymers such as polylysine and ethylenevinylacetate; other adhesion inducing agents such as monocyte chemotactic protein, fibroblast stimulating factor I, histamine, endothelin-1, angiotensin II, bromocriptine, methysergide, methotrexate, N-carboxybutyl chitosan, carbon tetrachloride, thioacetamide, quartz dust, fibrosin, and ethanol; or other molecules that stabilize thrombus formation or inhibit clot lysis for example proteins including Factor XIII, .alpha.2-antiplasmin, plasminogen activator inhibitor-1 (PAI-1) or the like; and anti-bacterial/anti-infective agents or antibiotic drugs like amoxicillin; ampicillin; benzylpenicillin; chloramphenicol; clindamycin; erythromycin; lincomycin; rifampicin or materials like silver or silver ions, colloidal silver, silver sulfadiazine, and/or silver nitrate.

In some examples, a therapeutic agent delivered by a nasal implant described herein may include one or more chemotherapy agents. For example, the therapeutic agent may include an Antracycline such as Doxorubicin (Adriamycin), Daunorubicin, Epirubicin, Idarubicin, orotherantitumor antibiotics such as Actinonycin-D, Bleomycin, Mitomycin-C. The therapeutic agent may also include an alkylating agent such as nitrogen mustards including mechloromethamine, chlorambucil, cyclophosphamide (Cytoxan), ifosfamide, melphalan; a nitrosourea such as streptozocin, carmustine (BNCU), lomustine; an alkyl sulfonate-such as busulfan; a triazine such asdacarbazine (DTIC) ortemozolomide (Temodar); anethylenimine such asthiotepa, altretamine (hexamethylmelamine). The therapeutic agent may also include one or more platinum drugs such as cisplatin, carboplatin, oxalaplatin. The therapeutic agent may also include an Antimetabolite such as 5-fluorouracil (5-FU), 6-mercaptopurine (6-MP), Capecitabine (Xeloda®), Cladribine, Clofarabine, Cytarabine (Ara-C®); Floxuridine, Fludarabine, Gemcitabine (Gemzar®), Hydroxyurea, Methotrexate, Pemetrexed (Alimta®), Pentostatin, or Thioguanine. The therapeutic agent may also include a topoisomerase inhibitor such astopotecan, rinotecan, etoposide, teniposide, or mitoxantrone. The therapeutic agent may also include a mitotic inhibitor, including one or more taxanes such as paclitaxel (Taxol®) and docetaxel (Taxotere®), one or more epothilones such as ixabepilone (Ixempra®), one or more vinca alkaloids such as vinblastine (Velban®), vincristine (Oncovin®), and vinorelbine (Navelbine®), or estramustine (Emcyt®). The therapeutic agent may also include L-asparaginase, proteasome inhibitors such as bortezomib, or others.

A delivered therapeutic agent may also include one or more corticosteroids such as prednisone, methylprednisolone (Solumedrol®), and dexamethasone (Decadron®). Suitable anti-inflammatory agents include but are not limited to, for example, nonsteroidal anti-inflammatory drugs (NSAIDs) such aspirin, celecoxib, choline magnesium trisalicylate, diclofenacpotasium, diclofenac sodium, diflunisal, etodolac, fenoprofen, flurbiprofen, ibuprofen, indomethacin, ketoprofen, ketorolac, melenamic acid, nabumetone, naproxen, naproxen sodium, oxaprozin, piroxicam, rofecoxib, salsalate, sulindac, and tolmetin; and corticosteroids such as cortisone, hydrocortisone, methylprednisolone, prednisone, prednisolone, betamethesone, beclomethasonedipropionate, budesonide, dexamethasone sodium phosphate, flunisolide, fluticasone propionate, triamcinolone acetonide, betamethasone, fluocinolone, fluocinonide, betamethasone dipropionate, betamethasone valerate, desonide, desoximetasone, fluocinolone, triamcinolone, triamcinolone acetonide, mometasone furoate, clobetasol propionate, and dexamethasone.

In some examples, a delivered therapeutic agent may include one or morehormone antagonist agents, such as for treatments including cancer, weight loss, menopause, acne treatment, etc. Such hormone antagonist agents may include but are not limited to: Aldosterone Antagonists, Androgen Antagonists, Antithyroid Agents, Calcimimetic Agents, Estrogen Receptor Modulators, Insulin Antagonists, Leukotriene Antagonists, Prostaglandin Antagonists.

Any suitable physiologically active substance or excipient can be delivered to a targeted body structure using implant devices described herein. Additional examples of such substances may include, but are not limited to, anti-inflammatory agents, anti-infective agents, anesthetics, pro-inflammatory agents, preservatives, cell proliferative agents, tretinoin, procoagulants, fillers, binders, surfactants, and the like. Anti-infective agents may include, but are not limited to, anthelmintics (mebendazole), antibiotics including aminoclycosides (gentamicin, neomycin, tobramycin), antifungal antibiotics (amphotericin b, fluconazole, griseofulvin, itraconazole, ketoconazole, nystatin, micatin, tolnaftate), cephalosporins (cefaclor, cefazolin, cefotaxime, ceftazidime, ceftriaxone, cefuroxime, cephalexin), beta-lactam antibiotics (cefotetan, meropenem), chloramphenicol, macrolides (azithromycin, clarithromycin, erythromycin), penicillins (penicillin G sodium salt, amoxicillin, ampicillin, dicloxacillin, nafcillin, piperacillin, ticarcillin), tetracyclines (doxycycline, minocycline, tetracycline), bacitracin; clindamycin; colistimethate sodium; polymyxin b sulfate; vancomycin; antivirals including acyclovir, amantadine, didanosine, efavirenz, foscarnet, ganciclovir, indinavir, lamivudine, nelfinavir, ritonavir, saquinavir, stavudine, valacyclovir, valganciclovir, zidovudine; quinolones (ciprofloxacin, levofloxacin); sulfonamides (sulfadiazine, sulfisoxazole); sulfones (dapsone); furazolidone; metronidazole; pentamidine; sulfanilamidumcrystallinum; gatifloxacin; and sulfamethoxazole/trimethoprim.

In various examples, therapeutic agents delivered using the implant devices described herein may include venoconstrictors/vasoconstrictors including, but are not limited to sodium, potassium, epinephrin, norepinephrine, phenylephrine, vasopressin, noradrenaline, and the like. Oxymetazoline (Afrin) is a decongestant that shrinks blood vessels in the nasal passages. Dilated blood vessels can cause nasal congestion (stuffy nose). In some cases, Oxymetazoline mixtures may be particularly suitable venoconstrictors, but any suitable venoconstrictor/vasoconstrictor may be employed.

Anesthetics may include, but are not limited to ethanol, bupivacaine, chloroprocaine, levobupivacaine, lidocaine, mepivacaine, procaine, ropivacaine, tetracaine, desflurane, isoflurane, ketamine, propofol, sevoflurane, codeine, fentanyl, hydromorphone, marcaine, meperidine, methadone, morphine, oxycodone, remifentanil, sufentanil, butorphanol, nalbuphine, tramadol, benzocaine, dibucaine, ethyl chloride, xylocaine, and phenazopyridine.

Other substances that can be delivered using the devices and examples disclosed herein include various pharmacological agents, excipients, venoconstrictors, and other substances well known in the art of pharmaceutical formulations. Other substances include, but are not limited to, antiplatelet agents, anticoagulants, coagulants, ACE inhibitors, cytotoxic agents, ionic and nonionic surfactants (e.g., Pluronic™, Triton™), detergents (e.g., polyoxyl stearate, sodium lauryl sulfate), emulsifiers, demulsifiers, stabilizers, aqueous and oleaginous carriers (e.g., white petrolatum, isopropyl myristate, lanolin, lanolin alcohols, mineral oil, sorbitan monooleate, propylene glycol, cetylstearyl alcohol), solvents like Dimethyl Sulfoxide (DMSO), preservatives (e.g., methylparaben, propylparaben, benzyl alcohol, ethylene diaminetetraacetate salts), thickeners (e.g., pullulin, xanthan, polyvinylpyrrolidone, carboxymethylcellulose), plasticizers (e.g., glycerol, polyethylene glycol), antioxidants (e.g., vitamin E), buffering agents, glues including but not limited to biocompatible cyanoacrylates, and the like.

In some examples, therapeutic agents delivered using implant devices described herein may include biocompatible and bioresorbable polymers such as those described, for example, in U.S. Pat. No. 6,423,085 to Murayama et al. and U.S. Pat. No. 6,676,971 to Goupil et al., the contents of which are hereby incorporated by reference in their entirety.

Such materials can include naturally occurring materials or materials derived from natural sources, or synthetic materials. Examples of biodegradable polymers which can be used include polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyhydroxyalkanoates (PHAs), polyalkylene oxalates, polyalkylene succinates, poly(malic acid), poly(amino acids), polyvinylpyrrolidone, polyethylene glycol, polyhydroxycellulose, chitin, chitosan, and copolymers, terpolymers, or combinations or mixtures of the above materials, with or without added components.

Proteins such as collagen, fibrinogen, fibronectin, vitronectin, laminin, thrombin, and gelatin may also be employed.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one example, the features and elements so described or shown can apply to other examples. It will also be appreciated by those of skill in the art that references to a structure or feature that is disposed "adjacent" another feature may have portions that overlap or underlie the adjacent feature.

Terminology used herein is for the purpose of describing particular examples only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative examples are described above, any of a number of changes may be made to various examples without departing from the scope of the invention as described by the claims. For example, the order in which various described method steps are performed may often be changed in alternative examples, and in other alternative examples one or more method steps may be skipped altogether. Optional features of various device and system examples may be included in some examples and not in others. Therefore, the foregoing description is provided primarily for exemplary purposes and should not be interpreted to limit the scope of the invention as it is set forth in the claims.

The examples and illustrations included herein show, by way of illustration and not of limitation, specific examples in which the subject matter may be practiced. As mentioned, other examples may be utilized and derived there from, such that structural and logical substitutions and changes may be made without departing from the scope of this disclosure. Such examples of the inventive subject matter may be referred to herein individually or collectively by the term "invention" merely for convenience and without intending to voluntarily limit the scope of this application to any single invention or inventive concept, if more than one is, in fact, disclosed. Thus, although specific examples have been illustrated and described herein, any arrangement calculated to achieve the same purpose may be substituted for the specific examples shown. This disclosure is intended to cover any and all adaptations or variations of various examples. Combinations of the above examples, and other examples not specifically described herein, will be apparent to those of skill in the art upon reviewing the above description.

What is claimed is:

1. A method of treating tissue in a nasal cavity, comprising:
   inserting a bioresorbable implant into a soft tissue of the nasal cavity, wherein the bioresorbable implant comprises:
   a porous bioresorbable tube defined by a wall formed from one or more porous bioresorbable polymers, the porous bioresorbable tube including pores and an interior bore that extends from a first end to a second end, and
   a pharmaceutical composition loaded in the wall of the porous bioresorbable tube and filling at least partially the interior bore of the porous bioresorbable tube; and after inserting the bioresorbable implant into the soft tissue of the nasal cavity, releasing the pharmaceutical composition from the bioresorbable implant, wherein the wall of the porous bioresorbable tube is configured to control a release rate of the pharmaceutical composition over time, the release rate is determined by:

(i) a release of the pharmaceutical composition loaded in the wall of the porous bioresorbable tube, wherein the release of the pharmaceutical composition loaded in the wall leaves channels in the wall, and (ii) a release of the pharmaceutical composition from the interior bore:

(a) via a degradation of the one or more porous bioresorbable polymers, (b) through the pores of the porous bioresorbable tube, and (c) through the channels left by the release of the pharmaceutical composition loaded in the wall of the porous bioresorbable tube, wherein the release of the pharmaceutical composition from the interior bore occurs more quickly as the pharmaceutical composition loaded in the wall of the porous bioresorbable tube is released.

2. The method of claim 1, wherein the one or more porous bioresorbable polymers comprise a plurality biodegradable polymers with different degradation rates such that releasing the pharmaceutical composition filling at least partially the interior bore comprises releasing the pharmaceutical composition filling at least partially the interior bore at a plurality of release rates, which are different from each other.

3. The method of claim 1, wherein the bioresorbable implant comprises a plurality of segments, and wherein each segment comprises a different biodegradable polymer such that releasing the pharmaceutical composition filling at least partially the interior bore comprises releasing the pharmaceutical composition filling at least partially the interior bore at a plurality of release rates that are different from each other.

4. The method of claim 1, wherein the bioresorbable implant comprises a tip having a pointed shape, and wherein inserting the bioresorbable implant into the soft tissue comprises piercing and penetrating the soft tissue using the tip of the bioresorbable implant.

5. The method of claim 4, wherein inserting the bioresorbable implant comprises inserting the bioresorbable implant in the soft tissue using a delivery device attached to a distal end of an endoscope.

6. The method of claim 1, wherein the pharmaceutical composition comprises at least one of:
one or more drugs, or
one or more therapeutic agents.

7. The method of claim 1, wherein the release of the pharmaceutical composition loaded in the wall of the porous bioresorbable tube is faster than the release of the pharmaceutical composition from the interior bore.

8. A bioresorbable implant for use in a nasal region, comprising:

a porous bioresorbable tube defined by a wall formed from one or more porous bioresorbable polymers, the porous bioresorbable tube including pores and an interior bore that extends from a first end to a second end; and a pharmaceutical composition loaded in the wall of the porous bioresorbable tube and filling at least partially the interior bore of the porous bioresorbable tube, wherein a release rate of the pharmaceutical composition from the bioresorbable implant is determined by:

(i) a release of the pharmaceutical composition loaded in the wall of the porous bioresorbable tube, wherein the release of the pharmaceutical composition loaded in the wall leaves channels in the wall, and (ii) a release of the pharmaceutical composition from the interior bore:

(a) via a degradation of the one or more porous bioresorbable polymers, (b) through the pores of the porous bioresorbable tube, and (c) through the channels left by the release of the pharmaceutical composition loaded in the wall of the porous bioresorbable tube, wherein the release of the pharmaceutical composition from the interior bore occurs more quickly as the pharmaceutical composition loaded in the wall of the porous bioresorbable tube is released.

9. The bioresorbable implant of claim 8, wherein the bioresorbable implant comprises a plurality of segments.

10. The bioresorbable implant of claim 8, wherein the bioresorbable implant comprises a tip having a pointed shape.

11. The bioresorbable implant of claim 8, wherein an end of the bioresorbable implant is flared.

12. The bioresorbable implant of claim 8, wherein the release of the pharmaceutical composition from the interior bore through the pores of the porous bioresorbable tube relates to at least one of a size or a quantity of the pores.

13. The bioresorbable implant of claim 8, wherein the bioresorbable implant includes a first cap coupled to the first end and/or a second cap coupled to the second end.

14. The bioresorbable implant of claim 8, wherein the release of the pharmaceutical composition loaded in the wall of the porous bioresorbable tube is faster than the release of the pharmaceutical composition from the interior bore.

15. A system, comprising:
a bioresorbable implant comprising:

a porous bioresorbable tube defined by a wall formed from one or more porous bioresorbable polymers, the porous bioresorbable tube including pores and an interior bore that extends from a first end to a second end; and a pharmaceutical composition loaded in the wall of the porous bioresorbable tube and filling at least partially the interior bore of the porous bioresorbable tube, wherein a release rate of the pharmaceutical composition from the porous bioresorbable tube is determined by:

(i) a release of the pharmaceutical composition loaded in the wall of the porous bioresorbable tube, wherein the release of the pharmaceutical composition loaded in the wall leaves channels in the wall, and (ii) a release of the pharmaceutical composition from the interior bore:

(a) via a degradation of the one or more porous bioresorbable polymers, (b) through the pores of the porous bioresorbable tube, and (c) through the channels left by the release of the pharmaceutical composition loaded in the wall of the porous bioresorbable tube, wherein the release of the pharmaceutical composition from the interior bore occurs more quickly as the pharmaceutical composition loaded in the wall of the porous bioresorbable tube is released; and a delivery device configured to insert the bioresorbable implant in a soft tissue of a nasal cavity.

16. The system of claim 15, wherein the delivery device comprises a needle having a lumen, and
wherein the bioresorbable implant is deliverable into the soft tissue via the lumen of the needle.

17. The system of claim 15, wherein the delivery device comprises an elongated shaft having a distal end releasably coupled to a proximal end of the bioresorbable implant.

18. The system of claim 17, wherein the bioresorbable implant comprises a tip having a pointed shape configured to pierce and penetrate the soft tissue.

19. The system of claim 15, wherein the release of the pharmaceutical composition loaded in the wall of the porous bioresorbable tube is faster than the release of the pharmaceutical composition from the interior bore.

* * * * *